US009339418B2

(12) United States Patent
Hamada

(10) Patent No.: US 9,339,418 B2
(45) Date of Patent: May 17, 2016

(54) APPARATUS AND METHOD FOR MANUFACTURING ABSORBENT ARTICLE

(75) Inventor: Akira Hamada, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 560 days.

(21) Appl. No.: 13/259,478

(22) PCT Filed: Mar. 29, 2010

(86) PCT No.: PCT/JP2010/055539
§ 371 (c)(1),
(2), (4) Date: Nov. 15, 2011

(87) PCT Pub. No.: WO2010/113854
PCT Pub. Date: Oct. 7, 2010

(65) Prior Publication Data
US 2012/0070254 A1 Mar. 22, 2012

(30) Foreign Application Priority Data

Apr. 3, 2009 (JP) ................................. 2009-091500

(51) Int. Cl.
*D04H 1/44* (2006.01)
*D04H 3/10* (2012.01)
(Continued)

(52) U.S. Cl.
CPC ..... *A61F 13/15764* (2013.01); *A61F 13/15699* (2013.01); *A61F 13/15723* (2013.01);
(Continued)

(58) Field of Classification Search
CPC .......... B23P 19/02; B23P 11/02; B23P 25/00; B23P 19/00; D04H 1/08; D04H 1/44; D04H 3/10; D04H 5/02; D04H 11/04; D04H 13/00; D04H 17/00; D04H 17/10; B29C 65/00; B32B 37/00; B31F 5/00; B65C 9/00; Y10T 29/53657; Y10T 29/49863; Y10T 29/49885; Y10T 29/53
USPC ......... 156/556, 559, 566, 494, 495, 496, 552, 156/567; 28/116, 118, 123; 29/235, 446, 29/458, 700
See application file for complete search history.

(56) References Cited

U.S. PATENT DOCUMENTS 4,767,487 A * 8/1988 Tomsovic, Jr. ................ 156/256
4,874,456 A * 10/1989 Takagi .......................... 156/471
(Continued)

FOREIGN PATENT DOCUMENTS

| CN | 1179871 C | 12/2004 |
|---|---|---|
| EP | 0 338 111 | 4/1988 |

(Continued)

OTHER PUBLICATIONS

Office Action or Search Report based on Chinese Application No. 201080014695.9 dated Apr. 16, 2013 (13 pgs).
(Continued)

*Primary Examiner* — Essama Omgba
*Assistant Examiner* — Darrell C Ford
(74) *Attorney, Agent, or Firm* — Brinks Gilson & Lione

(57) ABSTRACT

An apparatus for manufacturing an absorbent article having a first material and a second material includes (A) a holding body that includes a holding surface and that holds the first material with the holding surface and (B) a transfer section that transfers the first material to the second material by moving the holding body, that is holding the first material, to the second material. (C) The first material has a first portion and a second portion, the second portion having a thickness greater than that of the first portion in a thickness direction of the first material. (D) The holding surface has a first region and a second region, the second region being located at a position that is more recessed to an inner side than the first region in a height direction of the holding body. (E) The holding body holds the first material by causing the first portion to be held by suction on the first region and causing the second portion to be held by suction on the second region.

8 Claims, 13 Drawing Sheets

(51) Int. Cl.
*D04H 13/00* (2006.01)
*B23P 19/02* (2006.01)
*B23P 19/00* (2006.01)
*A61F 13/15* (2006.01)
*A61F 13/49* (2006.01)
*B65G 47/84* (2006.01)

(52) U.S. Cl.
CPC ..... *A61F13/15739* (2013.01); *A61F 13/49061* (2013.01); *A61F 2013/49063* (2013.01); *B65G 47/848* (2013.01); *Y10T 29/49863* (2015.01); *Y10T 29/49885* (2015.01); *Y10T 29/53* (2015.01); *Y10T 29/53657* (2015.01)

(56) References Cited

U.S. PATENT DOCUMENTS

| | | | | |
|---|---|---|---|---|
| 5,830,296 | A * | 11/1998 | Emenaker et al. | 156/219 |
| 5,837,087 | A * | 11/1998 | Ahr | 156/250 |
| 6,482,278 | B1 * | 11/2002 | McCabe et al. | 156/73.1 |
| 8,663,420 | B2 * | 3/2014 | Nakakado et al. | 156/297 |
| 8,669,412 | B2 * | 3/2014 | Fernkvist et al. | 604/383 |
| 8,735,647 | B2 * | 5/2014 | Schoelling | 604/380 |
| 9,084,697 | B2 * | 7/2015 | Piantoni et al. | |
| 2002/0125105 | A1 * | 9/2002 | Nakakado | 198/471.1 |
| 2003/0066609 | A1 * | 4/2003 | Calvert | 156/362 |
| 2003/0075277 | A1 * | 4/2003 | Vogt | A61F 13/15756 156/519 |
| 2003/0121614 | A1 * | 7/2003 | Tabor et al. | 156/552 |
| 2004/0035521 | A1 | 2/2004 | Nakakado et al. | |
| 2004/0089403 | A1 * | 5/2004 | Satoh | 156/160 |
| 2006/0032589 | A1 * | 2/2006 | Nakakado et al. | 156/494 |
| 2006/0184149 | A1 * | 8/2006 | Kasai et al. | 604/367 |
| 2009/0294044 | A1 * | 12/2009 | Gill | A61F 13/15601 156/256 |
| 2010/0249740 | A1 * | 9/2010 | Miyamoto et al. | 604/384 |
| 2012/0041405 | A1 * | 2/2012 | Alkmin et al. | 604/383 |
| 2012/0070254 | A1 * | 3/2012 | Hamada | 414/225.01 |
| 2012/0073760 | A1 * | 3/2012 | Hamada et al. | 156/475 |
| 2014/0115847 | A1 * | 5/2014 | Tomsovic et al. | 28/118 |
| 2015/0000820 | A1 * | 1/2015 | Ottery | 156/66 |

FOREIGN PATENT DOCUMENTS

| | | |
|---|---|---|
| EP | 1 228 987 A1 | 8/2002 |
| EP | 2 522 325 A1 | 11/2012 |
| EP | 2 554 143 A1 | 2/2013 |
| JP | 03-165762 | 7/1991 |
| JP | 2002-301679 | 10/2002 |
| JP | 2004-148040 | 5/2004 |
| JP | 2004-223238 | 8/2004 |
| JP | 2005-298193 | 10/2005 |
| JP | 2006-124045 | 5/2006 |
| JP | 2009-061045 | 3/2009 |
| WO | WO 01/44086 A1 | 6/2001 |

OTHER PUBLICATIONS

Office Action or Search Report based on Japanese Application No. 2009-091500 dated Apr. 17, 2013 (2 pgs).
International Search Report from corresponding PCT application No. PCT/JP2010/055539 dated May 18, 2010, 4 pages).
Office Action or Search Report and English translation based on Eurasia Application No. 201101443-/1 dated Jul. 9, 2013 (2 pgs).
European extended Search Report from corresponding European application No. 10758625.7 dated Oct. 5, 2015 (8 pgs).

* cited by examiner

EXAMPLE OF
PRESENT INVENTION

VARIANT

APPARATUS AND METHOD FOR MANUFACTURING ABSORBENT ARTICLE

RELATED APPLICATION

The present application is a 35 U.S.C. §371 national stage filing of International Patent Application No. PCT/JP2010/055539, filed Mar. 29, 2010, to which priority is claimed under 35 U.S.C. §120 and through which priority is claimed under 35 U.S.C. §119 to Japanese Priority Patent Application No. 2009-091500, filed Apr. 3, 2009.

TECHNICAL FIELD

The present invention relates to an apparatus and method for manufacturing an absorbent article. The present invention particularly relates to an apparatus and method for manufacturing an absorbent article including a first material and a second material.

BACKGROUND ART

An apparatus and method for manufacturing absorbent articles such as diapers from a plurality of materials are already known. There are such apparatus and method in which the first material is transferred to the second material by, for example, causing a holding body having a holding surface to hold one of a plurality of materials (first material) at the holding surface and, thereafter, moving the holding body with the first material held thereon towards the other material (second material). (E.g., see Patent Literatures 1 to 3).

CITATION LIST

Patent Literature

Patent Literature 1: JP-A-2004-148040
Patent Literature 2: JP-A-2004-223238
Patent Literature 3: JP-A-2005-298193

DISCLOSURE OF INVENTION

Problems to be Solved by the Invention

In some cases, the first material may include portions having different thicknesses in its thickness direction. Due to the difference in thickness, unevenness may be produced in one of the surfaces, which is on a side to be transferred, of the first material (i.e., the surface on a side opposing the second material and hereinafter referred to as a transfer surface). Even if it is attempted to transfer the first material to the second material with such unevenness, the transferring may not be performed properly.

The present invention has been made in view of such a problem and its object is, when causing the holding body to hold the first material having portions with different thicknesses in the thickness direction, to perform holding in such a manner that the later transferring is performed in an appropriate manner.

Means for Solving the Problems

In order to achieve the objects described above, a primary aspect of the invention is an apparatus for manufacturing an absorbent article having a first material and a second material, the apparatus including:

A) a holding body that includes a holding surface and that holds the first material with the holding surface; and
B) a transfer section that transfers the first material to the second material by moving the holding body, that is holding the first material, to the second material,
C) wherein the first material has a first portion and a second portion, the second portion having a thickness greater than that of the first portion in a thickness direction of the first material,
D) wherein the holding surface has a first region and a second region, the second region being located at a position that is more recessed to an inner side than the first region in a height direction of the holding body, and
E) wherein the holding body holds the first material by causing the first portion to be held by suction on the first region and causing the second portion to be held by suction on the second region.

Other features of the invention will be elucidated from the following description and the accompanying drawings.

Advantageous Effects of the Invention

According to an aspect of the invention, when holding the first material having portions with different thicknesses in the thickness direction by the holding body, holding can be performed in such a manner that the later transferring is performed properly.

MODE FOR CARRYING OUT THE INVENTION

Figure 1A:
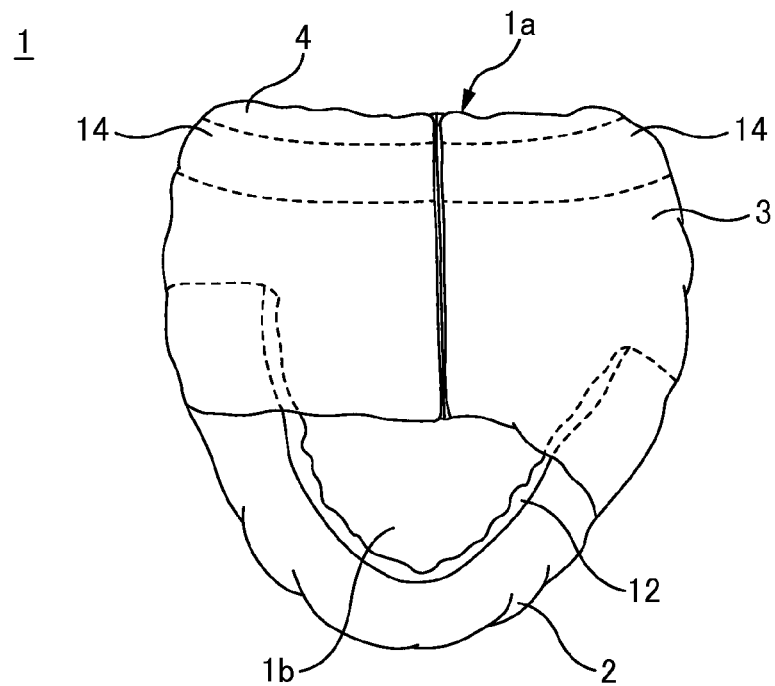
FIG. 1A is a side view of a diaper 1.

At least the following matters will be disclosed in the present specification and accompanying drawings.

First, there is provided an apparatus for manufacturing an absorbent article having a first material and a second material, the apparatus including:

A) a holding body that includes a holding surface and that holds the first material with the holding surface; and B) a transfer section that transfers the first material to the second material by moving the holding body, that is holding the first material, to the second material, C) wherein the first material has a first portion and a second portion, the second portion having a thickness greater than that of the first portion in a thickness direction of the first material, D) wherein the holding surface has a first region and a second region, the second region being located at a position that is more recessed to an inner side than the first region in a height direction of the holding body, and E) wherein the holding body holds the first material by causing the first portion to be held by suction on the first region and causing the second portion to be held by suction on the second region. With the apparatus for manufacturing an absorbent article described above, the first material can be held on the holding body while suppressing an occurrence of unevenness in a transfer surface of the first material. As a result, the first material held on the holding body can be properly transferred to the second material.

Further, in the apparatus for manufacturing the absorbent article described above, the absorbent article may include an absorbent main body as the first material, the absorbent main body may include an absorbent body and a gathering portion that is formed on each sides of the absorbent body, in an intersecting direction that intersects with a longitudinal direction of the absorbent main body, the first portion may be located at each end portions of the absorbent main body and the second portion being located at a central portion of the absorbent main body, the absorbent body may be disposed at the second portion, a stretchable member for forming the gathering portion may be attached to the first portion along the longitudinal direction, in a width direction of the holding surface, the first region may be located at both end portions of the holding surface and the second region being located at a central portion of the holding surface, and the holding body may hold the absorbent main body in such a manner that the width direction lies along the intersecting direction.

With such a configuration, the effect of the present invention becomes more significant. When the absorbent main body is placed on a flat holding surface, the stretchable member will contract and creases will be produced in the absorbent main body. With an occurrence of such creases, the later transferring will not be properly performed. On the other hand, with the configuration of the present embodiment, contraction of the absorbent main body can be suppressed and thus the absorbent main body can be properly transferred to the second material.

Further, in the apparatus for manufacturing the absorbent article described above, the second portion may extend along the longitudinal direction, the transfer portion may be a transfer drum that rotates while supporting the holding body, the transfer drum may rotate to thereby move the holding body from a receiving position at which the holding body receives the absorbent main body with the holding surface to a transfer position at which the absorbent main body held by the holding body is transferred to the second material, and the holding body may be provided in such a manner that, at the receiving position, the width direction lies along an axis of rotation of the transfer drum, and, at the transfer position, the width direction lies along a circumferential direction of the transfer drum.

With such a configuration, an effect of the present invention becomes more significant. In other words, in a case where the transferring is performed with the width direction of the holding surface lying along the circumferential direction of the transfer drum, a region of the absorbent main body which is transferred to the second material at the beginning of the transferring will become greater as compared to a case in which the transferring is performed with the width direction lying along the axis of rotation of the transfer drum. Even under such a condition, the absorbent main body held on the holding body can be appropriately transferred to the second material.

Further, in the apparatus for manufacturing the absorbent article described above, a level difference between the first region and the second region may be greater than or equal to a thickness difference between the first portion and the second portion. With such a configuration, the transfer surface of the absorbent body can be easily made flat and the absorbent body held on the holding body can be more properly transferred to the second material.

Further, in the apparatus for manufacturing the absorbent article described above, the holding body may hold the absorbent main body in such a manner that the second portion is placed inside an outer edge of the second region. With such a configuration, the transfer surface of the absorbent body can be even more easily made flat and the absorbent body held on the holding body can be even more properly transferred to the second material.

Further, in the apparatus for manufacturing the absorbent article described above, each end portion of the second region in the width direction may be inclined in such a manner that a length in the height direction becomes greater as it gets nearer to an end in the width direction. With such a configuration, the second portion can be prevented from being caught at a border between the first region and the second region at the time of transferring and thus the transferring can be performed smoothly.

Further, in the apparatus for manufacturing the absorbent article described above, the holding surface may have a plurality of holes formed therein, a suction mechanism may be provided, the suction mechanism being configured to suck the air through the holes in order that the holding body causes the first portion to be held by suction to the first region and causes the second portion to be held by suction to the second region, and among the plurality of holes, the hole formed in the second region may have a size that is smaller than a size of the hole formed in the first region. With such a configuration, since the suction force exerted on the second portion becomes smaller than the suction force exerted on the first portion, at the time of transferring, the second portion can be easily removed from the second region and the first material will be smoothly delivered to the second material (the transferring is performed smoothly).

Further, it is also possible to realize a method of manufacturing an absorbent article having a first material and a second material, the method comprising:

A) manufacturing the first material that has a first portion and a second portion, the second portion having a thickness greater than that of the first portion in a thickness direction of the first material;

B) causing a holding body that includes a holding surface to hold the first material with the holding surface; and C) transferring the first material to the second material by moving the holding body, that is holding the first material, to the second material, D) wherein, in the causing of the holding body to hold the first material, the holding body is caused to hold the first material by causing the first portion to be held by suction on a first region in the holding surface and causing the second portion to be held by suction on a second region, the second region being located at a position that is more recessed to an inner side than the first region in a height direction of the holding body. With such a method, when causing the holding body to hold the first material having portions with different thicknesses in the thickness direction, the holding can be performed in such a manner that the later transferring will be performed properly.

===Absorbent Article of the Present Invention===

In the present embodiment, by taking a diaper 1 as an example of an absorbent article, an apparatus and a method of manufacturing the diaper 1 will be described. In other words, a diaper manufacturing apparatus 30 described later corresponds to an example of an apparatus for manufacturing an absorbent article and a method of manufacturing the diaper 1 (hereinafter referred to as a manufacturing method of the diaper 1) corresponds to an example of a method of manufacturing an absorbent article.

<<Structure of Diaper 1>>

Figure 1B:
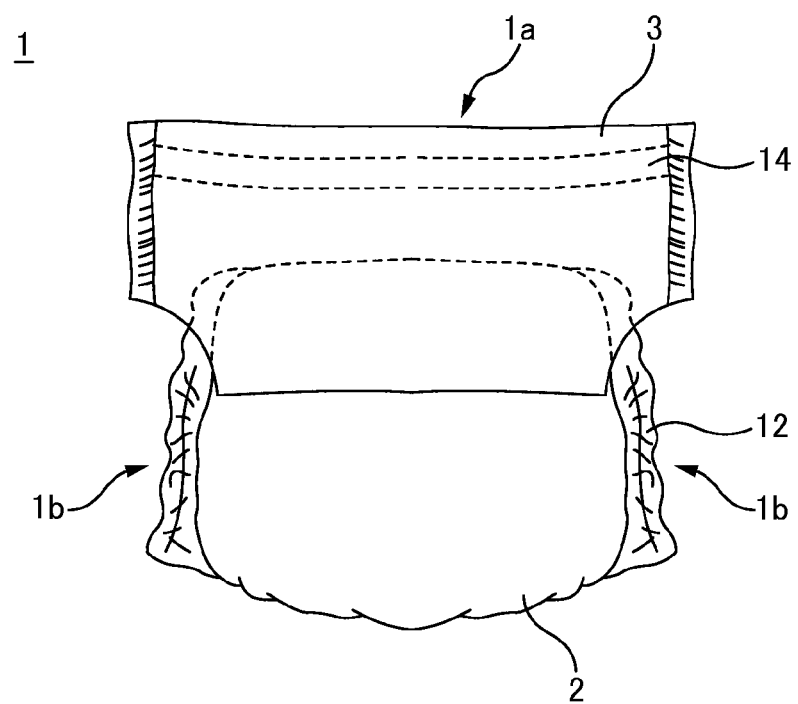
FIG. 1B is a rear view of the diaper 1.
Figure 1C:
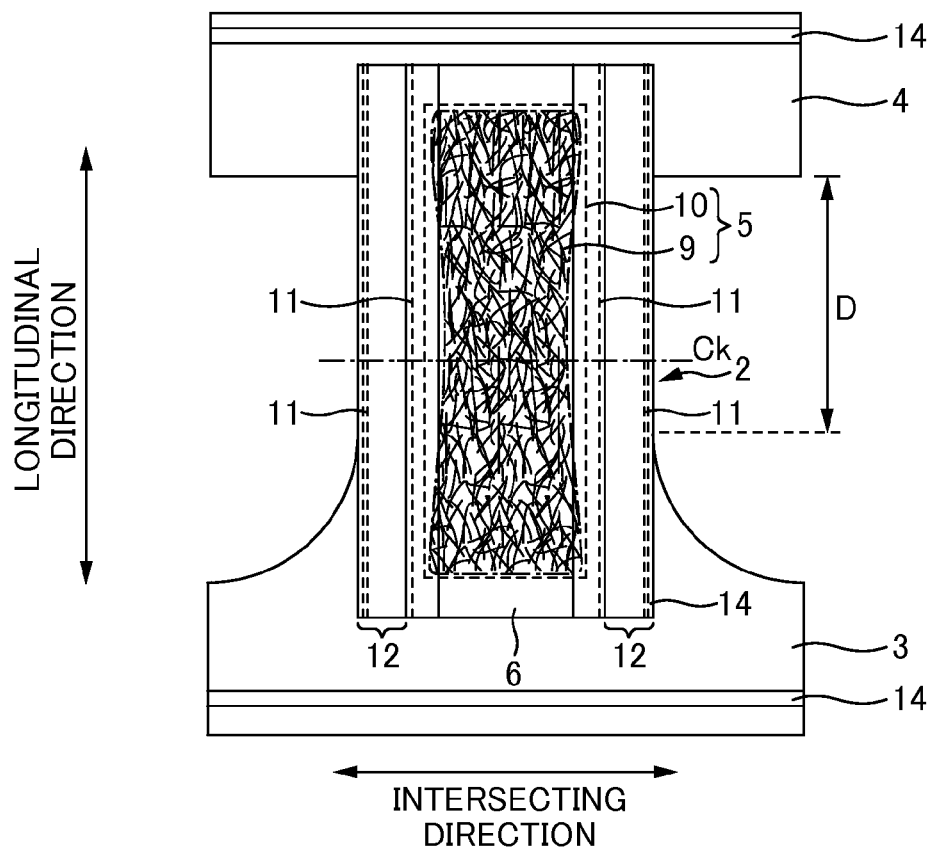
FIG. 1C is a diagram showing the diaper 1 in a spread out fashion.
Figure 2A:
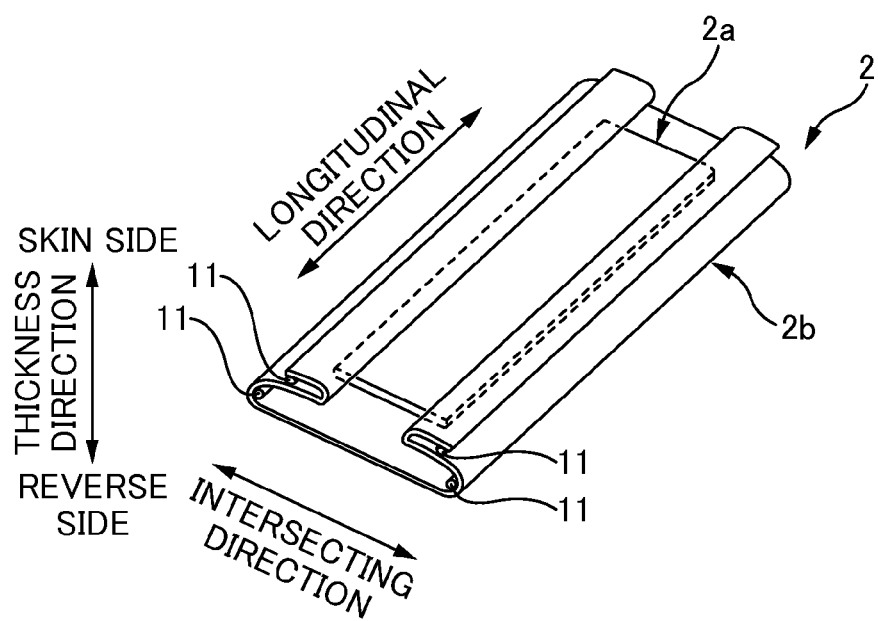
FIG. 2A is a perspective view of an absorbent main body 2.
Figure 2B:
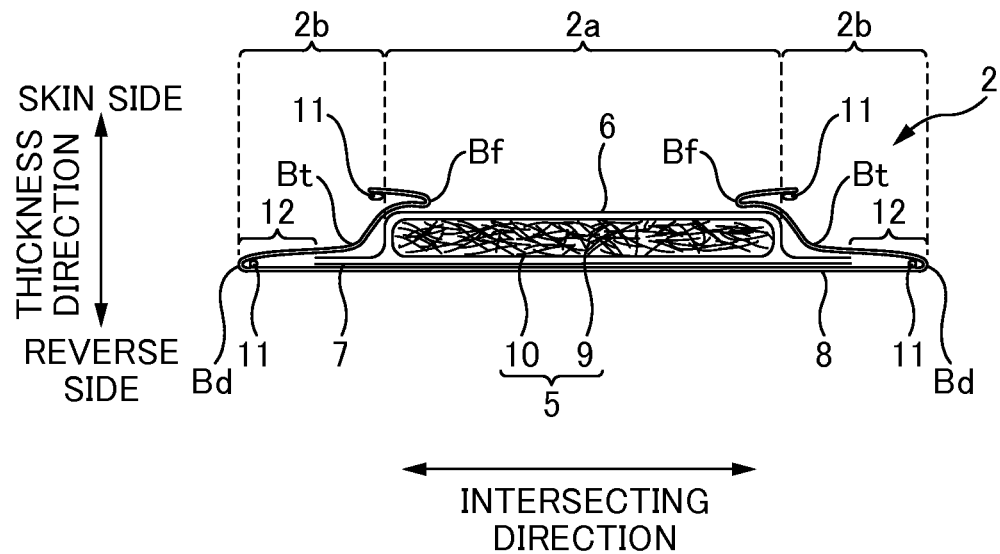
FIG. 2B is a cross section of the absorbent main body 2 at the center in the longitudinal direction thereof.

First, the structure of the diaper 1 will be described with reference to FIGS. 1A to 1C, 2A and 2B. FIG. 1A is a side view of the diaper 1 and FIG. 1B is a rear view of the diaper 1. FIG. 1C is a diagram showing the diaper 1 in a spread out fashion (a view seen from a side which comes into contact with a wearer's skin). FIG. 2A is a perspective view of an absorbent main body 2. FIG. 2B is a cross section of the absorbent main body 2 at the center in the longitudinal direction thereof. It is to be noted that in FIGS. 1C, 2A and 2B, a longitudinal direction of the absorbent main body 2, a direction intersecting with the longitudinal direction (hereinafter referred to as an intersecting direction) and a thickness direction are indicated by arrows, respectively.

The diaper 1 includes the absorbent main body 2 that comes into contact with the crotch of the wearer and absorbs body fluid such as urine, a back-side band 3 that covers a back-side part of the wearer and a stomach-side band 4 that covers a stomach-side part of the wearer. In a spread out state shown in FIG. 1C, the back-side band 3 and the stomach-side band 4 are provided in parallel with a distance D therebetween and the absorbent main body 2 bridges them in such a manner that a contour is substantially H-shaped when viewed in a planar view. Starting from such a state, the diaper 1 is folded in half at a folding position Ck that is located at the center in the longitudinal direction of the absorbent main body 2. The bands 3 and 4 which oppose each other in such a two-fold state are connected into an annular shape by being fastened at portions which are to come into contact with the wearer's flank. Thus, the diaper 1 comes to a wearing state in which a waist opening 1a and a pair of leg openings 1b are formed (see FIGS. 1A and 1B).

As for the fastening structure described above, in a case where a non-releasable joining structure such as welding is adopted, it becomes a pants-type product, and, in a case where a releasable joining structure such as a fastening tape (not shown) is adopted, it becomes an open-type product. In FIGS. 1A and 1B, a pants-type product is illustrated by way of example. In the following, constituent elements of the diaper 1 will be described.

The absorbent main body 2 is a member having a substantially rectangular shape in a planar view, and, as shown in FIG. 2A, a central portion thereof is somewhat more projected towards a skin surface side (a side that comes into contact with the skin of the wearer in the thickness direction) than a peripheral portion. That is to say, the absorbent main body 2 of the present embodiment includes portions with different thicknesses in its thickness direction.

Specifically, a raised portion 2a that is somewhat raised towards a skin side (a side which comes into contact with the wearer's skin) is provided at a central portion of the absorbent main body 2 and a thin portion 2b thinner than the raised portion 2a is provided at a portion surrounding the periphery of the raised portion 2a. The thin portion 2b corresponds to a first portion of the present invention. The raised portion 2a corresponds to a second portion of the present invention and it is a portion having a greater thickness in the thickness direction than the thin portion 2b (the first portion). In the direction intersecting with the longitudinal direction of the absorbent main body 2, the raised portion 2a is located at the central portion of the absorbent main body 2 and the thin portion 2b is located at each end portion of the absorbent main body 2. Further, the raised portion 2a extends along the longitudinal direction of the absorbent main body 2 and a length in such direction is slightly shorter than a length in the longitudinal direction of the absorbent main body 2.

Main constituent elements of the absorbent main body 2 are, as shown in FIG. 2B, an absorbent body 5, a front surface sheet 6 (top sheet) that covers the absorbent body 5 from the side of the skin, a reverse surface sheet 7 (back sheet) that covers the absorbent body 5 from the opposite side (reverse side) of the top sheet 6 and an exterior sheet 8 (outer sheet) that forms an exterior of the diaper 1 at a position further to the reverse side than the reverse surface sheet 7.

The absorbent body 5 is comprised of an absorbent body core 9 that is liquid absorbent fiber such as pulp fiber formed into a substantially gourde shape in a planar view and a thin paper 10 such as tissue paper that wraps it. The absorbent body core 9 may contain super absorbent polymer (SAP). The front surface sheet 6 is a liquid permeable nonwoven sheet and has a planar size greater than that of the absorbent body 5. The back surface sheet 7 is a non-liquid-permeable film sheet and has a planar size greater than that of the absorbent body 5. The absorbent body 5 is placed at the central portion of the absorbent main body 2 while being sandwiched between the front surface sheet 6 and the back surface sheet 7 and both of the above-mentioned sheets 6 and 7 are attached to each other in a frame-like manner at a portion extending outwardly beyond four sides of the absorbent body 5. That is to say, the absorbent body 5 is disposed at the above-mentioned raised portion 2a and a thickness of the raised portion 2a is greater than that of the thin portion 2b by a thickness of the absorbent body 5.

The exterior sheet 8 is a nonwoven sheet and has a planar size greater than that of the front surface sheet 6 or the back surface sheet 7. A portion of the exterior sheet 8 that extends outwardly in the intersecting direction is folded over towards an inner side and overlapping portions are joined together at a position near a folded over portion Bd. Further, in the vicinity of the folded over portion Bd, a stretchable member 11 such as a rubber thread is fixed in an extended state along the longitudinal direction of the absorbent main body 2. Thus, a leg-surrounding gathering portion 12 that produces stretchability at the leg opening 1b of the diaper 1 is formed at each side of the absorbent body 5 (i.e., both end sides in the intersecting direction of the absorbent main body 2.) Here, the leg-surrounding gathering portion 12 is an example of the gathering portion of the present invention and the stretchable member 11 is for forming the gathering portion. The stretchable member 11 is attached in an extended state to the absorbent main body 2 at each end portion in the intersecting direction corresponding to the above-mentioned thin portion 2b.

Figure 3:
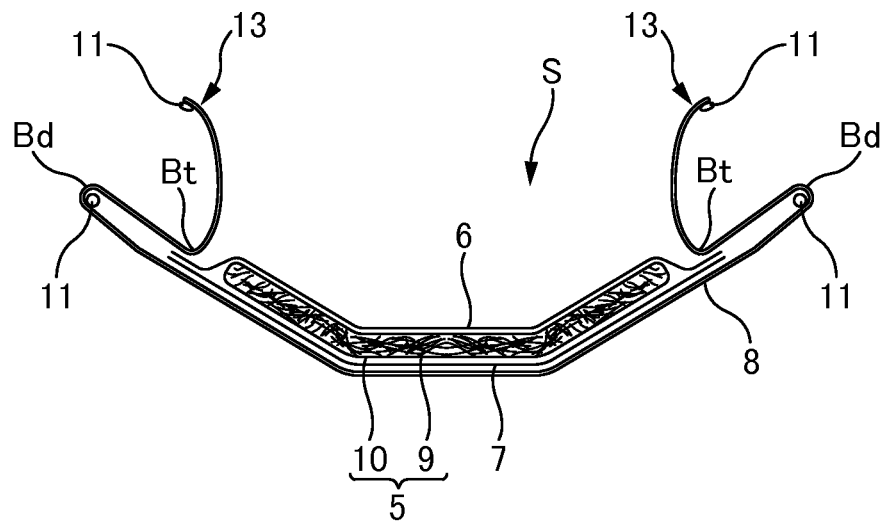
FIG. 3 is a cross-sectional diagram showing a three-dimensional gathering portion 13 of the diaper 1 when worn.

Further, the exterior sheet 8 that is folded over at a fold over portion Bd somewhat rises at a rising portion Bt placed inwardly from the fold over portion Bd and a portion of the rising portion that overlays the absorbent body 5 (to be more precise, the front surface sheet 6 that covers the absorbent body 5) is folded over again towards an outer side in the intersecting direction. In the vicinity of an end of a portion which has been folded over at such folded over portion Bf (a free end), the stretchable member 11 is fixed in an extended state along the longitudinal direction of the absorbent main body 2. Accordingly, a three-dimensional gathering portion 13 is formed on the absorbent main body 2 at a position where each end portion in the intersecting direction (transverse direction) of the absorbent body 5 is located. When the diaper 1 is being worn, the three-dimensional gathering portion 13 flexes back with the rising portion Bt being the point of support, comes into contact with a portion near an inguinal part of the wearer by rising up as shown in FIG. 3, and forms an accommodating space S that accommodates excretion between the three-dimensional gathering portion 13. FIG. 3 is a cross-sectional diagram showing the three-dimensional gathering portion 13 of the diaper 1 that is being worn.

The leg-surrounding gathering portion 12 and the three-dimensional gathering portion 13 are not limited to structures in which they are formed on the exterior sheet 8, but may also be formed on a material other than the exterior sheet 8 (e.g., a sheet member that is joined to the skin surface of the exterior sheet 8).

The back-side band 3 and the stomach-side band 4 are flexible sheets such as nonwoven fabrics and each of them is cut in a substantially rectangular shape in a plan view and intersects (substantially orthogonal to) the longitudinal direction of the absorbent main body 2. At the central portion in the longitudinal direction of each of the bands 3 and 4, an end portion in the longitudinal direction of the absorbent main body 2 that bridges the bands 3 and 4 is attached and fixed. In a case where each of the bands 3 and 4 is composed of a two-ply nonwoven fabric, the end portion in the longitudinal direction of the absorbent main body 2 may be fixed by being sandwiched between the nonwoven fabrics. Also, each of the bands 3 and 4 may be given a stretchability by fixing a rubber member 14 such as a rubber thread or a rubber band (see FIG. 1C) to each band 3, 4 in an extended state along the longitudinal direction of the bands 3 and 4. Further, a corner portion of the band 3 and 4 may be die cut in a substantially fan shape (gouge cut) so as to improve the fit of a portion forming the leg-surrounding gathering portion 12 of the band 3, 4 against a thigh of the wearer. In the present embodiment, among the bands 3 and 4, only the back-side band 3 is die cut, however, it is not limited thereto, and the stomach-side band 4 may also be die cut.

<<Manufacturing Method of Diaper 1>>

Figure 4:
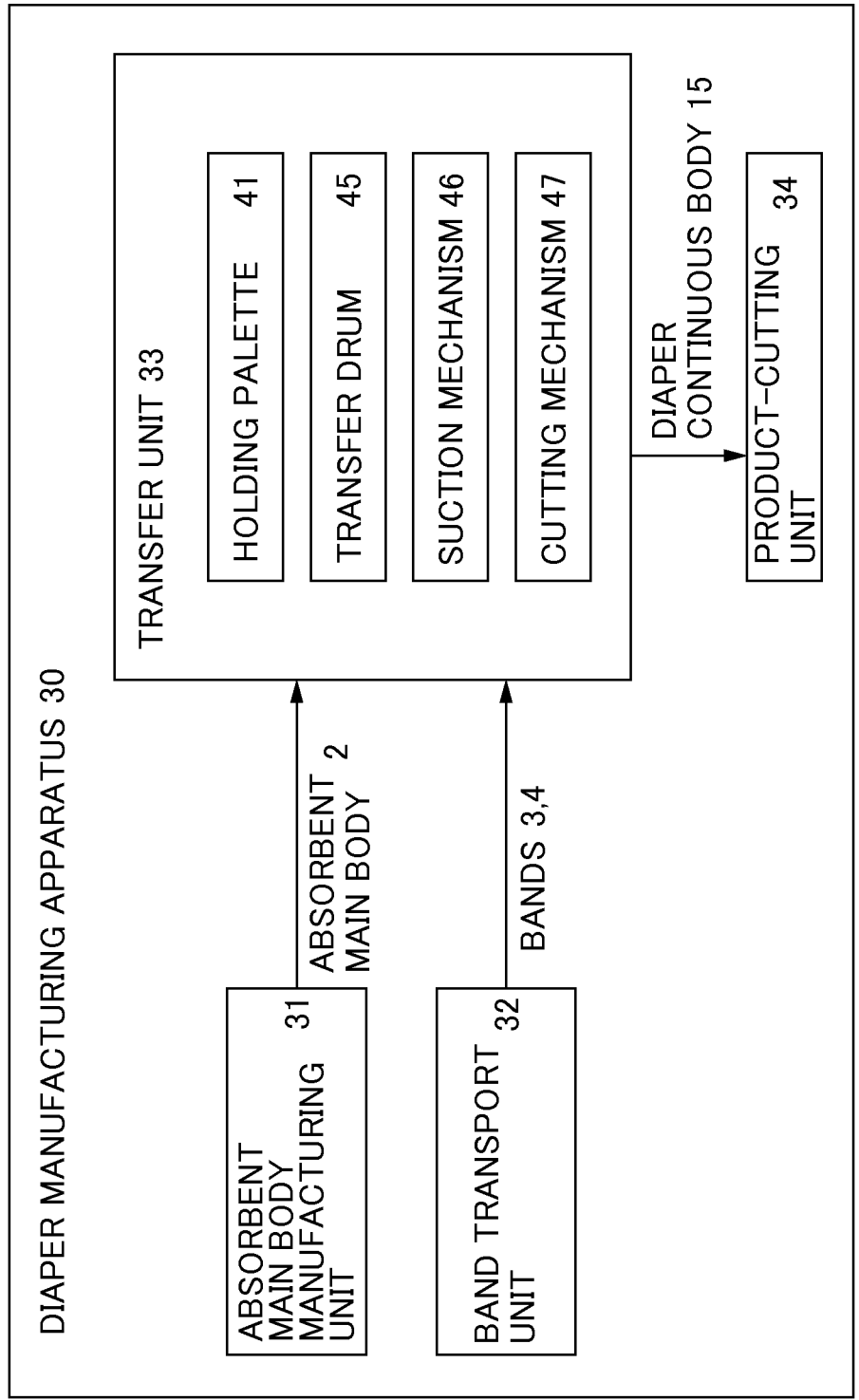
FIG. 4 is a block diagram illustrating main constituent elements of a diaper manufacturing apparatus 30.
Figure 5:
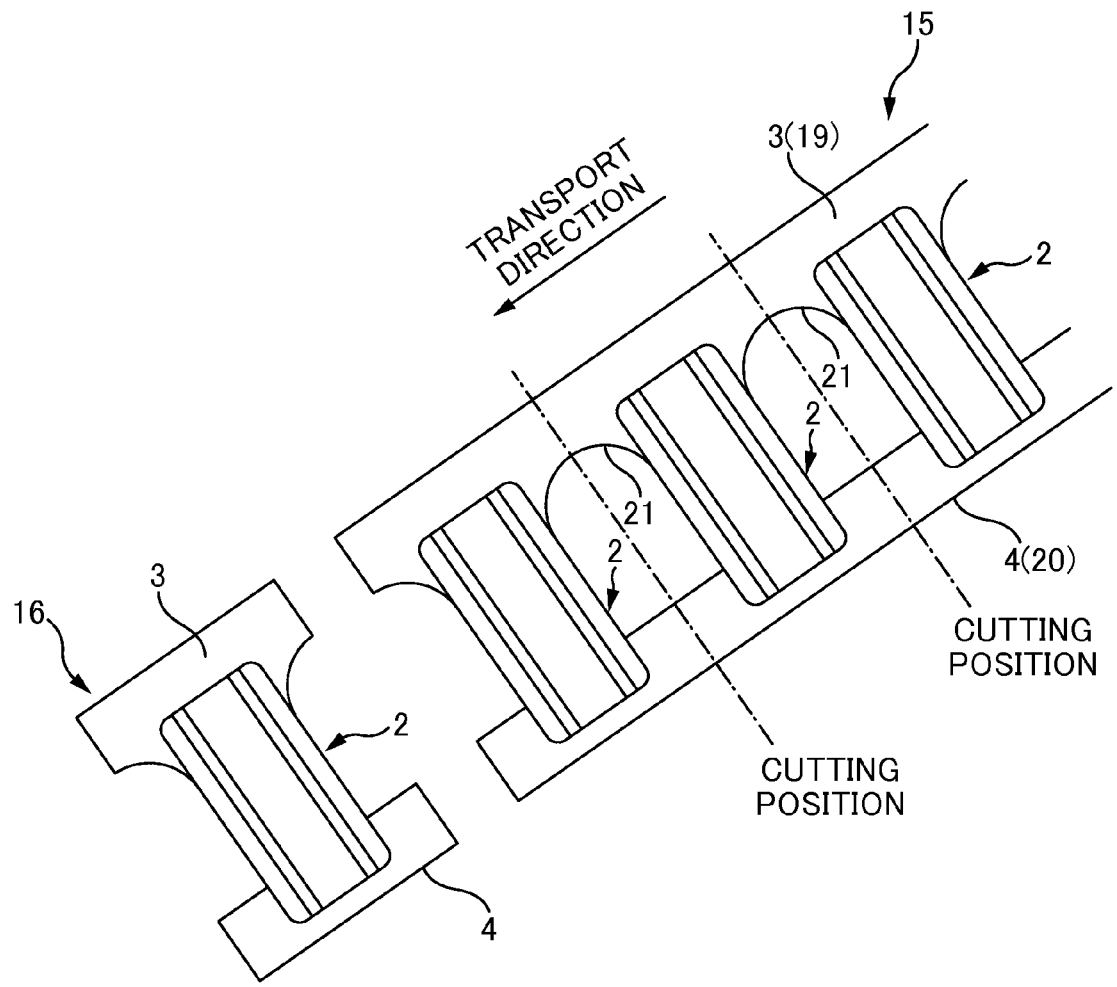
FIG. 5 is a diagram illustrating a diaper continuous body 15.
Figure 6A:
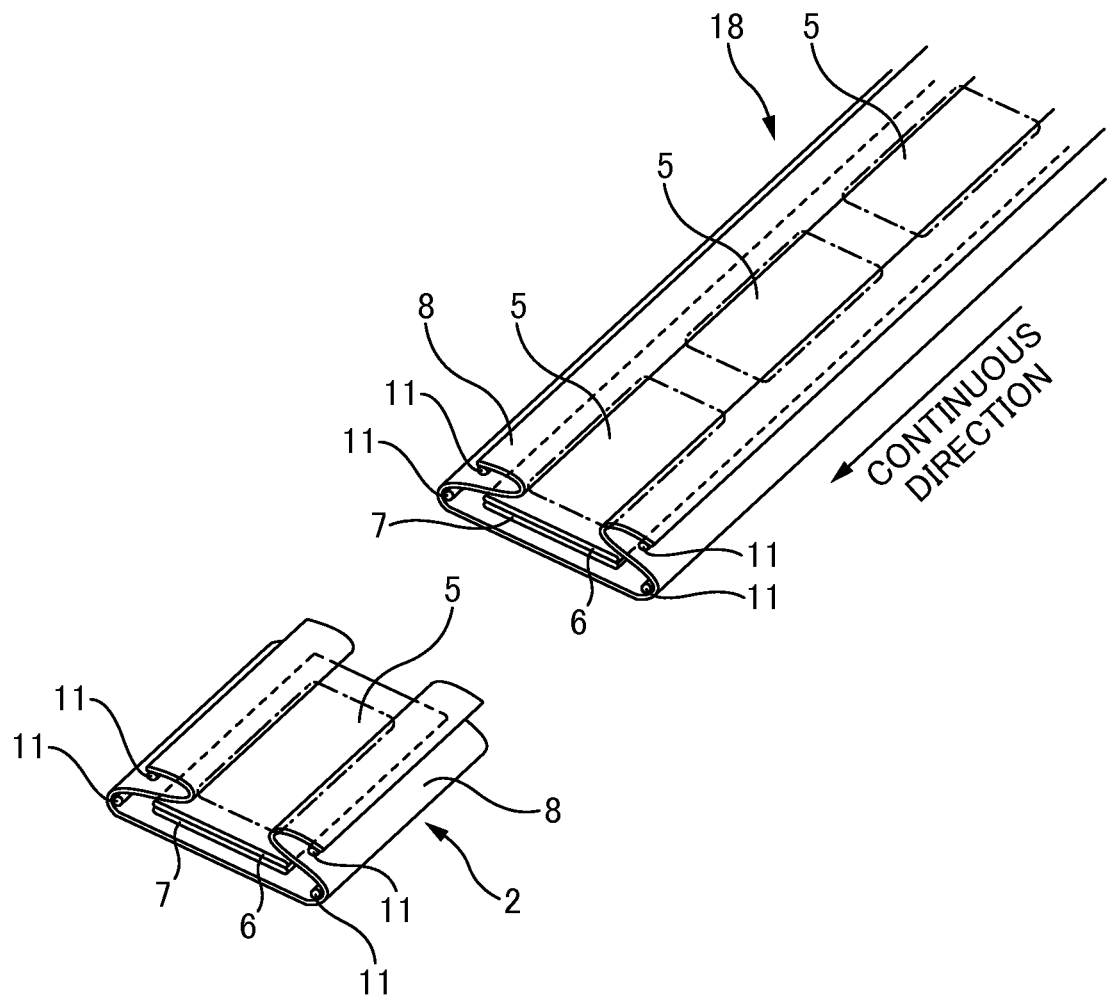
FIG. 6A is a diagram illustrating a manufacturing process of the diaper 1 (part 1).
Figure 6B:
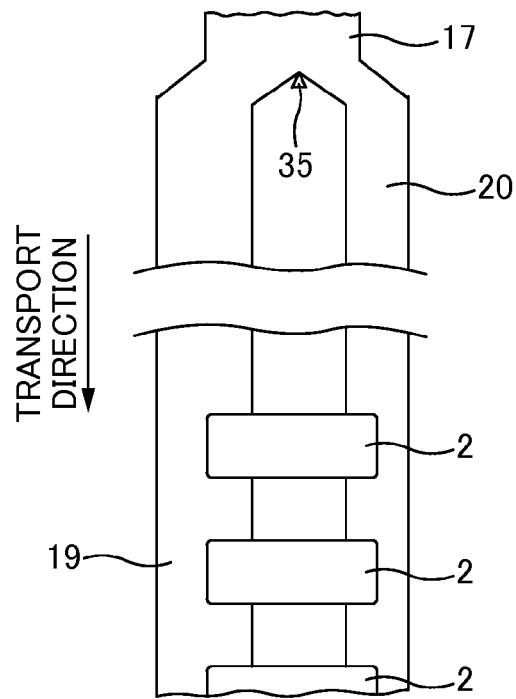
FIG. 6B is a diagram illustrating the manufacturing process of the diaper 1 (part 2).
Figure 6C:
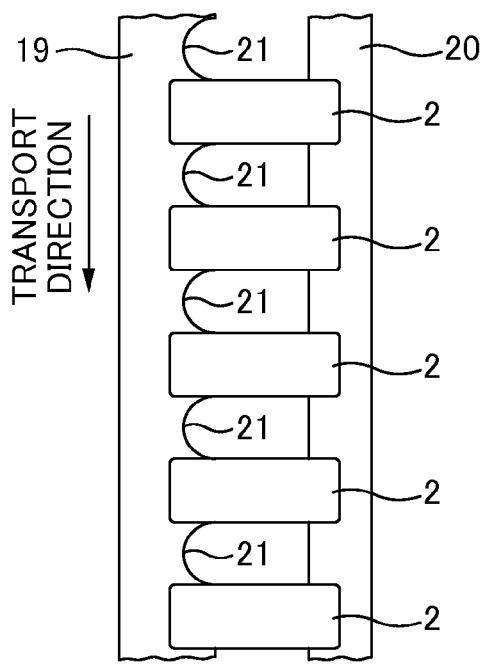
FIG. 6C is a diagram illustrating the manufacturing process of the diaper 1 (part 3).

Next, referring to FIGS. 4 to 6C, the method of manufacturing the diaper 1 will be described. FIG. 4 is a block diagram illustrating main constituent elements of a diaper manufacturing apparatus 30. FIG. 5 is a diagram illustrating a diaper continuous body 15. FIGS. 6A to 6C are diagrams illustrating a manufacturing process of the diaper 1. For the simplification of illustration, the absorbent main body 2 is illustrated in a simplified manner in FIGS. 6A and 6C.

The method of manufacturing the diaper 1 according to the present embodiment is a method of continuously manufacturing the diaper 1 as a product and is performed by the diaper manufacturing apparatus 30. As shown in FIG. 4, the diaper manufacturing apparatus 30 includes an absorbent main body manufacturing unit 31, a band transport unit 32, a transfer unit 33, a product-cutting unit 34, etc.

The absorbent main body manufacturing unit 31 is a unit that manufactures the absorbent main body 2 by combining each of the constituent elements of the absorbent main body 2 (i.e., absorbent body 5, front surface sheet 6, back surface sheet 7, exterior sheet 8, etc.) That is to say, the manufacturing method of the diaper 1 according to the present embodiment includes a step of manufacturing the absorbent main body 2 by the absorbent main body manufacturing unit 31 (hereinafter referred to as an absorbent main body manufacturing step). In the absorbent main body manufacturing step, the front surface sheet 6, the back surface sheet 7 and the exterior sheet 8 are respectively reeled out from a state of being wound in a roll and joined together, and also the absorbent body 5 (specifically, the absorbent body core 9 wrapped in the thin paper 10) is sandwiched between the front surface sheet 6 and the back surface sheet 7. As a result, in the absorbent main body manufacturing step, the absorbent main body 2 having the above-mentioned raised portion 2a and the thin portion 2b is manufactured.

It is to be noted that each sheet 6, 7, 8 is reeled out in a continuous fashion and the absorbent body 5 is disposed at a regular interval in its continuous direction (sandwiched between the front surface sheet 6 and the back surface sheet 7). Also, at a predetermined portion of the exterior sheet 8, the above-mentioned stretchable member 11 is fixed in an extended state along the continuous direction of the exterior sheet 8. Further, the absorbent body 5 that is sandwiched between the front surface sheet 6 and the back surface sheet 7 is placed on the exterior sheet 8 and, after the stretchable member 11 has been fixed at the predetermined position, it is folded back at a predetermined fold back portions (the fold back portions Bd, Bf described above). Accordingly, the above-mentioned leg-surrounding gathering portion 12 and the three-dimensional gathering portion 13 are formed on the exterior sheet 8.

At the time the above-mentioned series of processes are completed, the absorbent main body manufacturing step terminates. At such time, a continuous body 18 is formed that continues in such a manner that the absorbent main bodies 2 are provided in series along the longitudinal direction thereof (see FIG. 6A). This continuous body 18 is transported towards a transfer step at a later stage while maintaining its continuous state, and upon starting the transfer step, it is cut into a product unit and separated into individual absorbent main body 2.

The band transport unit 32 is a unit that transports the bands 3, 4 towards the transfer step. Each band 3, 4 is transported in a state of a continuous band 19 and 20, respectively, that continues along the transport direction (see FIG. 6B). In the present embodiment, as shown in FIG. 6B, a pre-split continuous band 17 having a slightly greater width is torn in the wide direction by a splitter 35 and splits into the continuous band 19 of the back-side band 3 and the continuous band 20 of the stomach-side band 4. The continuous bands 19, 20 after being separated are transported in a substantially parallel manner with a distance between them being the same as the distance D between the bands 3 and 4 at the time of completion of the product.

The transfer unit 33 is a unit that transfers the absorbent main body 2, which is a single body obtained by cutting the continuous body 18 of the absorbent main body 2 supplied from the absorbent main body manufacturing step into a product unit, to a pair of bands 3 and 4 that is transported in the state of continuous bands 19 and 20 from the band transport unit 32. That is to say, the method of manufacturing the diaper 1 of the present embodiment includes a step of transferring the absorbent main body 2 to each band 3, 4 by the transfer unit 33 (hereinafter referred to as a transfer step). Here, the absorbent main body 2 corresponds to the first material and each band 3, 4 corresponds to an example of the second material.

In the transfer step, as shown in FIG. 6B, the absorbent main body 2 bridges the bands 3, 4 that are transported in the state of the continuous bands 19 and 20 at a regular interval along the transport direction of the bands 3, 4. At this time, each absorbent main body 2 is, at each of its end portions in the longitudinal direction, joined to each band 3, 4. Then, as a result of the plurality of absorbent main bodies 2 being sequentially joined to the bands 3, 4, the pair of bands 3, 4 and the bridging absorbent main bodies 2 will form a ladder shape. It is to be noted that in the present embodiment, although an adhesion joining using a hot-melt adhesive is adopted as a method of joining the absorbent main body 2 to the bands 3 and 4, other methods such as compression bonding such as emboss compression bonding can also be used.

Thereafter, each band 3, 4 is further transported in the transport direction, and during such transportation, a die cut process is applied to the continuous band 19 of the back-side band 3. This die cut process is a process of cutting out a portion of the continuous band 19 of the back-side band 3, which portion being positioned between neighboring absorbent main bodies 2, and is performed by a die cut unit which is not illustrated in the drawings. After the die cut process has been performed, the continuous band 19 of the back-side band 3 is cut out in a substantially semicircular shape at a regular interval in its continuous direction and a substantially arcuate arch 21 is formed at such cut out portions (see FIG. 6C).

After having completed the steps described above, the diaper continuous body 15 (see FIG. 5) which continues in such a manner that the diapers 1 in a spread out fashion are disposed in series is formed. This diaper continuous body 15 is transported towards the product-cutting step at a later stage while keeping the continuing state. In such product-cutting step, the product-cutting unit 34 cuts the diaper continuous body 15 into a product unit by a cutter that is not illustrated in the drawings. Then, after having performed a final process on the diaper continuous body piece 16 that has been cut (see FIG. 5), (for example, in the case of a pants-type product, the diaper continuous body piece 16 is folded in half at a folding position Ck and the bands 3 and 4 are fastened by being connected into an annular shape such as by welding), the diaper 1 as a product is completed.

===Transfer Step by Transfer Unit 33===

In this part, the above-described transfer unit 33 and the transfer step will be further described.

<<Flow of Transfer Step>>

Figure 7:
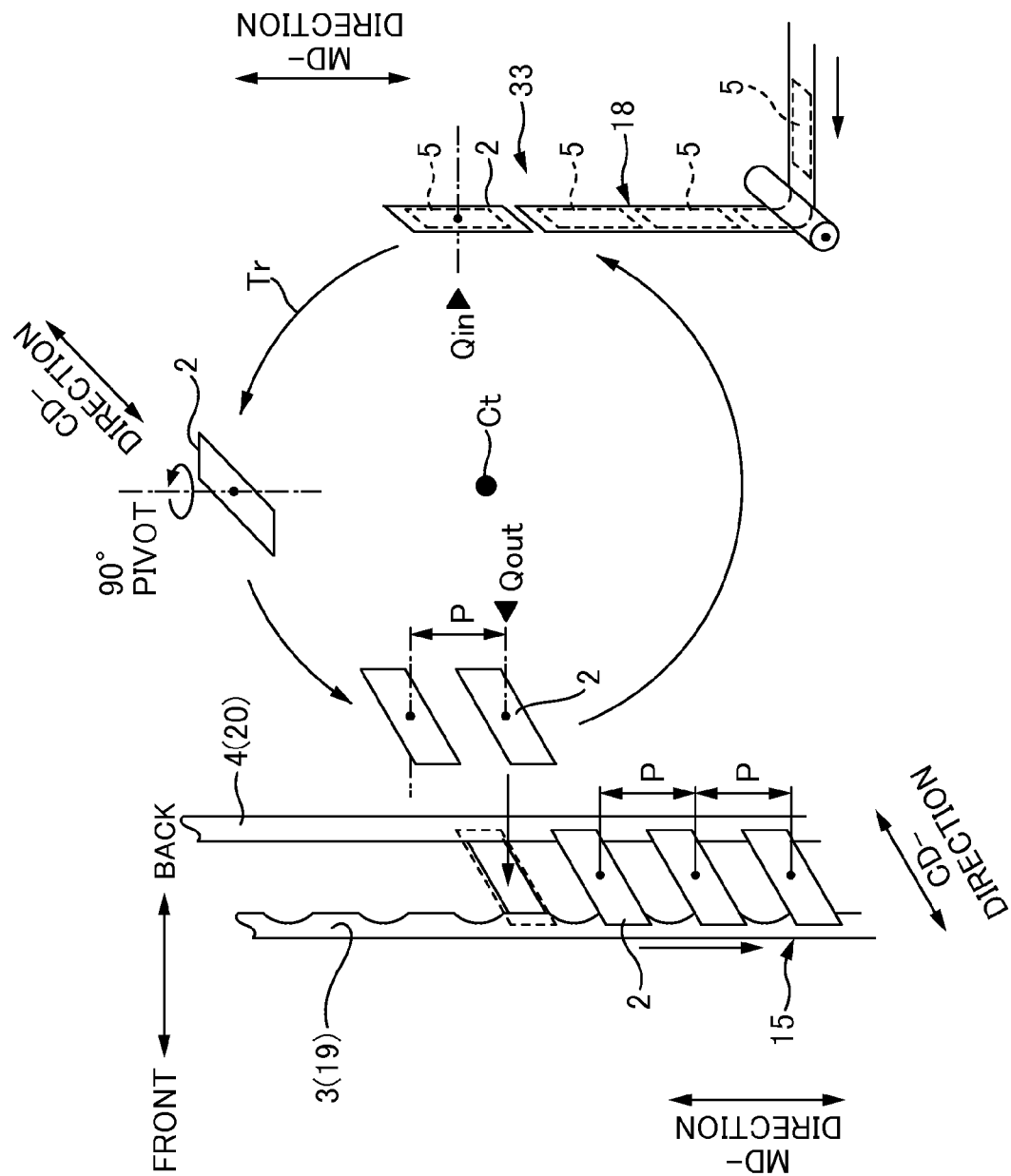
FIG. 7 is a schematic diagram showing each process performed in a transferring step.

First, a general flow of the transfer step will be described with reference to FIG. 7. FIG. 7 is a schematic diagram showing each process performed in the transferring step. It is to be noted that, in FIG. 7, in order to facilitate the understanding of the explanation, each material is illustrated in a somewhat simplified manner. For example, at the point of being inputted into the transfer step, the absorbent main body 2 has the leg-surrounding gathering portion 12 and the three-dimensional gathering portion 13 formed thereon, but they are not shown in FIG. 7.

In the transfer step, while transporting the bands 3 and 4 forming a pair and provided parallel to each other with a distance D in a direction substantially orthogonal to the transport direction (specifically, the bands 3 and 4 in the state of the continuous bands 19 and 20) along the transport direction, the absorbent main bodies 2 are bridged and attached sequentially to the bands 3 and 4. Hereinafter, a direction corresponding to a device-width direction of the transfer unit 33 is referred to as a CD-direction and any direction in a plane orthogonal to the CD-direction is referred to as an MD-direction. That is to say, in the present embodiment, the direction in which the bands 3 and 4 are aligned corresponds to the CD-direction and the transport direction corresponds to the MD-direction.

When developing the transfer step, the transfer unit 33 firstly cuts the continuous body 18 of the absorbent main body 2 supplied from the absorbent main body manufacturing step into a product unit (specifically, cut at a substantially central position between the absorbent bodies 5 neighboring in the continuous direction of the continuous body 18). Accordingly, the absorbent main body 2 as a single body is produced by dividing the continuous body 18 of the absorbent main body 2. At this time, the longitudinal direction of the absorbent main body 2 lies along the MD-direction (see FIG. 7).

The absorbent main body 2 that has been divided from the continuous body 18 as a single body in the manner above is received by a holding palette 41, which will be described later, at a receiving position Qin and thereafter moves together with the holding palette 41 towards the pair of bands 3 and 4. That is to say, the transfer unit 33 moves the absorbent main body 2 to the transferring position Qout in order to transfer the absorbent main body 2 received at the receiving position Qin to the pair of bands 3 and 4. It is to be noted that as shown in FIG. 7, the absorbent main body 2 moves along a circumferential track Tr centering on a predetermined axis (specifically, an axis of rotation Ct of the transfer drum 45 to be described later).

As shown in FIG. 7, the absorbent main body 2 pivots through 90° (degrees) about the center of the plane while moving from the receiving position Qin to the transferring position Qout. Thus, it changes from a state in which the longitudinal direction of the absorbent main body 2 lies along the MD-direction to a state in which it lies along the CD-direction. Then, when the absorbent main body 2 reaches the transferring position Qout, each end portion in the longitudinal direction of the absorbent main body 2 will be attached and fixed to each band 3, 4 that is in a state of the continuous bands 19 and 20 and passing the transferring position Qout in the MD-direction. (I.e., the absorbent main body 2 is transferred to the bands 3 and 4). It is to be noted that, in transferring the absorbent main body 2 to the bands 3 and 4, a back-side surface 2d (see FIG. 9B) that is on the opposite side of the skin-side surface 2c (a surface on the side which comes into contact with the wearer's skin when the diaper 1 is worn (see FIG. 9B)) in its thickness direction is made to oppose the bands 3 and 4, and each end portion in the longitudinal direction of the back-side surface 2d will be attached to the bands 3 and 4. That is to say, the back-side surface 2d corresponds to a surface on a side where the absorbent main body 2 is to be transferred (transfer surface).

As a result of the above-steps being repeated, the absorbent main bodies 2 will sequentially bridge the bands 3 and 4 with a predetermined pitch P in the MD-direction and thus the above-mentioned substantially ladder shaped diaper continuous body 15 will be formed. That is to say, the absorbent main body 2 will be transferred to the bands 3 and 4 at a regular interval along the MD-direction with its longitudinal direction being substantially orthogonal to the MD-direction. It is to be noted that the pitch P between the absorbent main bodies 2 is pre-adjusted to a distance corresponding to a product specification (product size) of the diaper 1.

<<Structure of Transfer Unit 33>>

Figure 8:
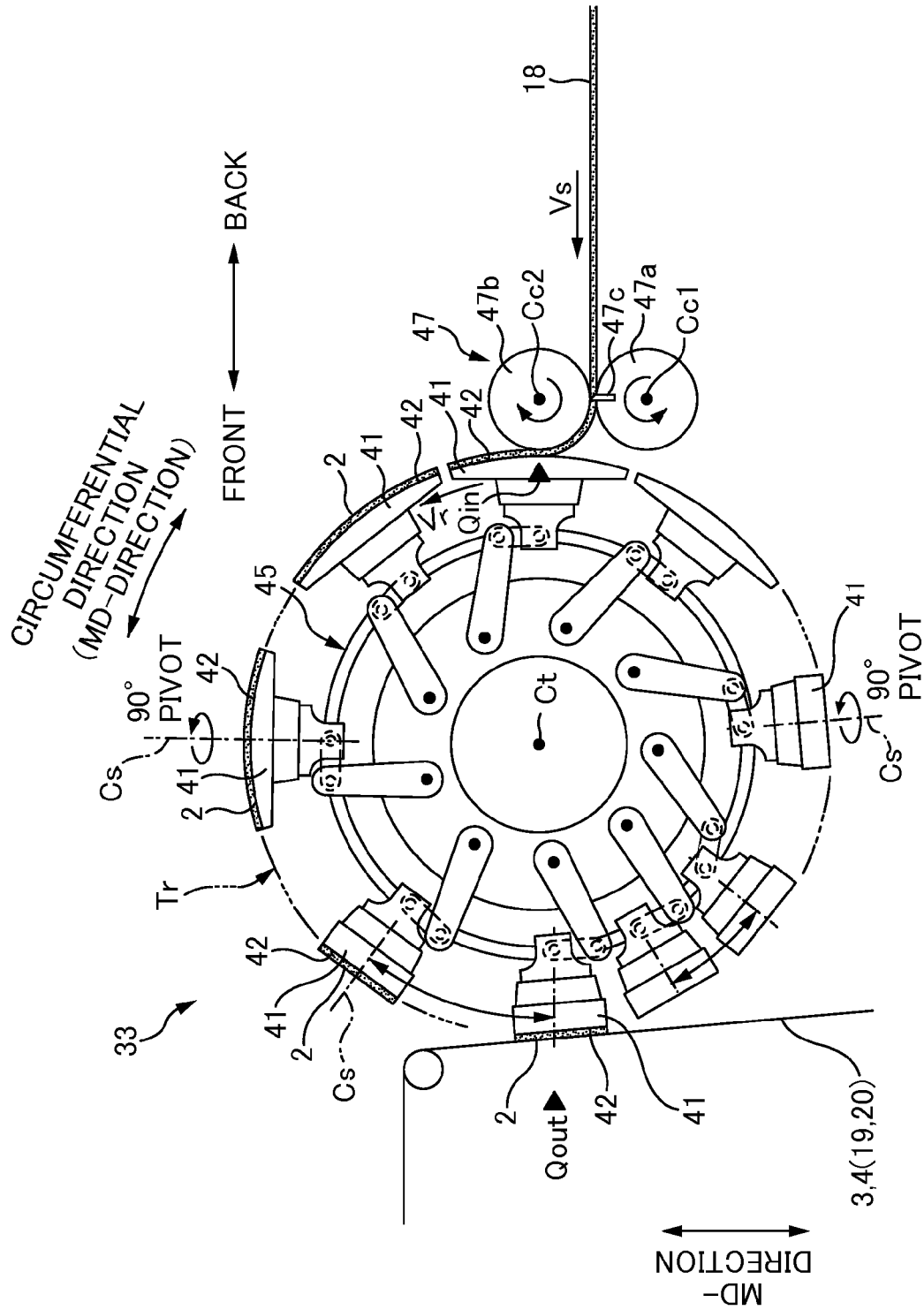
FIG. 8 is a side view of a transfer unit 33.

The transfer unit 33 performs the transport step in a procedure described above. As shown in FIG. 8, the transfer unit 33 includes a transfer drum 45 that rotates about the axis of rotation Ct that lies along the CD-direction and a plurality of holding palettes 41 (nine holding pallets in the example shown in FIG. 8) that is arranged along the circumferential direction of the transfer drum 45 while being supported by the transfer drum 45. FIG. 8 is a diagram showing the transfer unit 33 when viewed from the side. It is to be noted that, in FIG. 8, the CD-direction is a direction that penetrates the plane of paper.

Further, the transfer unit 33 includes a suction mechanism 46 that performs a suction operation for maintaining a holding state of the absorbent main body 2 at the holding palette 41 (see FIG. 4) and a cutting mechanism 47 that cuts the continuous body 18 of the absorbent main body 2 into a product unit (see FIG. 8). Hereinafter, each constituent elements of the transfer unit 33 will be described.

<Cutting Mechanism 47>

As shown in FIG. 8, the cutting mechanism 47 includes a pair of upper and lower rollers 47a and 47b that is located at a position directly before the receiving position Qin of the absorbent main body 2 in the circumferential direction of the transfer drum 45. The pair of upper and lower rollers 47a and 47b rotates about axes Cc1 and Cc2, respectively, which lie along the CD-direction with outer peripheral surfaces opposing each other. One of the rollers 47a (lower roller 47a) of the pair of rollers 47a and 47b is a cutter roller having a flat blade 47c provided on its outer peripheral surface. The other roller 47b (upper roller 47b) is an anvil roller whose outer peripheral surface is a smooth surface and that receives the above-mentioned flat blade 47c.

By causing the continuous body 18 of the absorbent main body 2, which is being supplied from the absorbent main body manufacturing step, to pass between the pair of upper and lower rollers 47a and 47b, a predetermined portion of the continuous body 18 (specifically, a portion corresponding to the cutting position) will be pinched between the flat blade 47c provided on the lower roller 47a and the outer peripheral surface of the upper roller 47b. Thereby, the absorbent main body 2 of a designed length will be divided and produced from a tip portion (a downstream end portion) of the continuous body 18. It is to be noted that the continuous body 18 of the absorbent main body 2 passes between the rollers 47a and 47b in a state where its continuous direction lies along the MD-direction. Therefore, the absorbent main body 2 will be, at the point where it is divided and produced from the continuous body 18 by being cut, in a state where its longitudinal direction lies along the MD-direction (specifically, the circumferential direction of the transfer drum 45).

<Holding Palette 41, Transfer Drum 45 and Suction Mechanism 46>

As shown in FIG. 8, each of the plurality of holding palettes 41 includes a holding surface 42 facing outward in the radial direction of the transfer drum 45, and it is a plate member of a substantially rectangular parallelepiped shape that holds the absorbent main body 2 at the holding surface 42 and corresponds to the holding body of the present invention. After having received the absorbent main body 2 that has been divided and produced from the continuous body 18 at the receiving position Qin, the holding palette 41 keeps holding the absorbent main body 2 in surface contact with the holding surface 42 until the absorbent main body 2 reaches the transferring position Qout. It is to be noted that with the absorbent main body 2 being held on the holding surface 42, the skin-side surface 2c of the absorbent main body 2 comes into contact with the holding surface 42 and the reverse-side surface 2d faces outward in the radial direction of the transfer drum 45 (see FIGS. 9B and 9C).

Further, as shown in FIG. 8, the holding palette 41 is pivotable about the pivotal axis Cs that passes through the center of plane of the holding surface 42 and lies along the radial direction of the transfer drum 45. Accordingly, the absorbent main body 2 that is held by the holding surface 42 can be changed from the state in which its longitudinal direction lies along the MD-direction to the state in which its longitudinal direction lies along the CD-direction. Further, the holding palette 41 is individually supported in such a manner that it is reciprocable relative to the transfer drum 45 in the same direction as a rotational direction of the transfer drum 45. As a result, by changing the distance between the holding palettes 41 that are adjacent to each other in the circumferential direction of the transfer drum 45, this holding palette 41 and the adjacent holding palette 41 can be prevented from interfering with each other, for example, when the holding palette 41 is pivoted about the pivotal axis Cs.

The transfer drum 45 is a main body of the transfer unit 33 and it is a barrel of a substantially cylindrical shape corresponding to the transfer section. Explaining in detail, the transfer drum 45 transfers the above-mentioned absorbent main body 2 to the above-mentioned bands 3 and 4 by moving each of the holding palettes 41 holding the absorbent main body 2 towards the bands 3 and 4. Further explaining in detail, the transfer drum 45 rotates about the axis of rotation Ct while supporting the plurality of holding palettes 41. Accordingly, while holding the absorbent main body 2 received at the receiving position Qin on the holding surface 42, each of the holding palettes 41 revolves in a counterclockwise direction along a round circumferential track Tr about the axis of rotation Ct. Then, the holding palette 41 that has reached the transferring position Qout on the circumferential track Tr delivers the absorbent main body 2 to the bands 3 and 4 that pass by the position Qout in the state of the continuous bands 19 and 20.

As has been described above, by rotating about the axis of rotation Ct, the transfer drum 45 moves each of the holding palettes 41 holding the absorbent main body 2 from the receiving position Qin to the transferring position Qout along the circumferential track Tr. It is to be noted that the receiving position Qin is a position on the circumferential track Tr at which the holding palette 41 receives the absorbent main body 2 from the cutting mechanism 47 on the holding surface 42. The transferring position Qout is a position on the circumferential track Tr at which the absorbent main body 2 held on the holding palette 41 is transferred to the bands 3, 4 (delivered from the holding palette 41 to the bands 3, 4) and, in the present embodiment, it is a position that is rotated through approximately 180 degrees from the receiving position Qin in the circumferential direction of the transfer drum 45 (i.e., the rotational direction of the transfer drum 45 and corresponds to the MD-direction.)

The suction mechanism 46 performs a suction operation for keeping a good holding state of the absorbent main body 2 on the holding surface 42 while the holding palette 41 moves from the receiving position Qin to the transferring position Qout along the circumferential track Tr. This suction operation is an operation in which the air is sucked (drawn) through a plurality of holes 42a (see FIG. 9A) formed over the entire surface of the holding surface 42. Accordingly, when the absorbent main body 2 is placed on the holding surface 42, its skin-side surface 2c (a surface on a side that does not oppose the bands 3, 4 at the time of transfer in the thickness direction of the absorbent main body 2) will be held by suction on the holding surface 42. That is to say, the holding palette 41 cooperates with the suction mechanism 46 to hold the absorbent main body 2 while holding the absorbent main body 2 on the holding surface 42 by suction. Here, the holding of the absorbent main body 2 by suction means that the absorbent main body 2 is pulled towards the holding surface 42 and includes, not only a case of pulling in such a manner that the entire surface of the skin-side surface 2c comes into contact with the holding surface 42 but also a case of pulling in such a manner that a part of the skin-side surface 2c does not come into contact with the holding surface 42 but a major part thereof comes into contact with the holding surface 42.

Figure 9A:
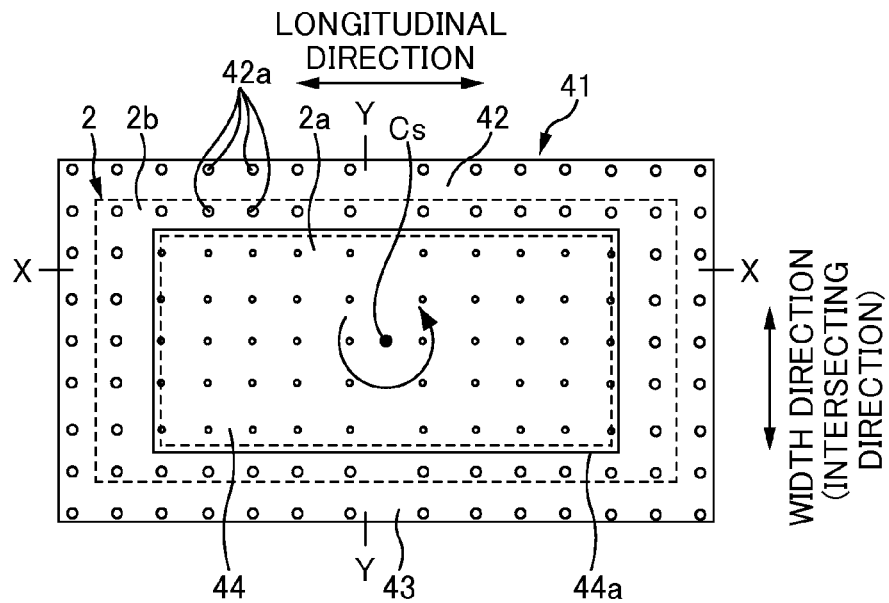
FIG. 9A is a plan view of a holding palette 41.
Figure 9B:
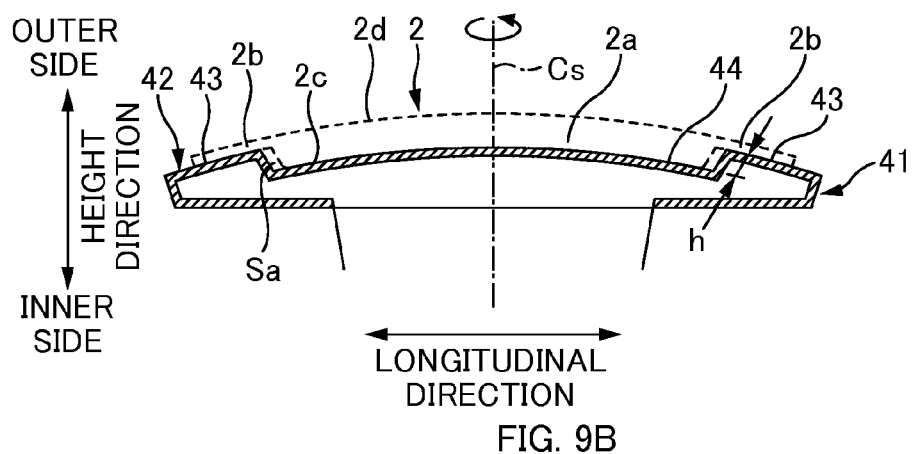
FIG. 9B is a cross-sectional diagram taken along X-X in FIG. 9A.
Figure 9C:
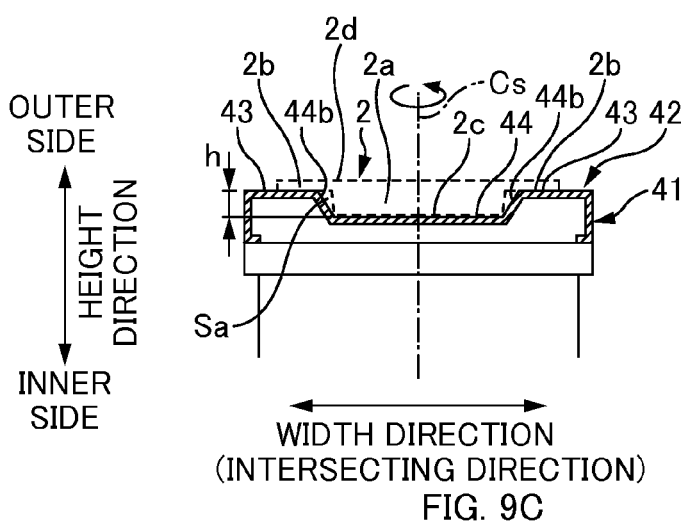
FIG. 9C is a cross-sectional diagram taken along Y-Y in FIG. 9A.

Now, referring to FIGS. 9A to 9C, the holding palette 41 will be described in detail. FIG. 9A is a plan view of the holding palette 41. FIG. 9B is a cross-sectional diagram taken along X-X in FIG. 9A. FIG. 9C is a cross-sectional diagram taken along Y-Y in FIG. 9A. It is to be noted that in each of the figures described above, the absorbent main body 2 held by the holding palette 41 is shown by broken lines.

The holding palette 41 is a hollow substantially rectangular parallelepiped (see FIGS. 9B and 9C). The longitudinal direction of the holding palette 41 matches with the longitudinal direction of the holding surface 42 and is substantially orthogonal to the width direction of the holding surface 42 (see FIG. 9A). In other words, the width direction of the holding surface 42 intersects with (substantially orthogonal to) the longitudinal direction of the holding surface 42. Further, the holding palette 41 is supported by the transfer drum 45 with its height direction lying along the radial direction of the transfer drum 45.

Here, while positioned at the receiving position Qin, the holding palette 41 is in a state where the longitudinal direction of the holding surface 42 lies along the MD-direction (specifically, the circumferential direction of the transfer drum 45). In other words, it is in such a manner that the width direction of the holding surface 42 lies along the direction of the axis of rotation (direction of the axis of rotation Ct) of the transfer drum 45. Accordingly, the holding palette 41 can securely hold the absorbent main body 2 received from the cutting mechanism 47 at the receiving position Qin with the holding surface 42. Explaining in detail, at the receiving position Qin, the holding palette 41 receives the absorbent main body 2 in a state where the longitudinal direction of the absorbent main body 2 and the longitudinal direction of the holding surface 42 are both lying along the MD-direction. Therefore, the holding palette 41 will hold the absorbent main body 2 in such a manner that the longitudinal direction of the holding surface 42 lies along the longitudinal direction of the absorbent main body 2 (i.e., in a state where the width direction of the holding surface 42 lies along the intersecting direction that intersects with the longitudinal direction of the absorbent main body 2). As a result, the holding palette 41 can hold the absorbent main body 2 in such a manner that the absorbent main body 2 is stable on the holding surface 42. It is to be noted that the planar size of the holding surface 42 is slightly greater than the planar size of the absorbent main body 2 (see FIG. 9A).

Further, as shown in FIG. 9B, the holding surface 42 is a curved surface whose ridge lines in the longitudinal direction are curved in an arcuate manner and its radius of curvature is substantially the same as the radius of the circumferential track Tr. Therefore, a moving velocity (rotational velocity) Vr of the holding palette 41 at the receiving position Qin can be maintained at a uniform velocity for the entire length in the longitudinal direction of the holding palette 41. With the moving velocity Vr being set so as to match a moving velocity Vs of the continuous body 18 of the absorbent main body 2, the holding palette 41 can receive the absorbent main body 2 at the receiving position Qin while preventing an occurrence of creases over the entire region in the longitudinal direction of the absorbent main body 2.

Further, the holding surface 42 of the present embodiment has regions positioned at mutually different positions in the height direction of the holding palette 41. Explaining in detail, as shown in FIG. 9A, the holding surface 42 has a first region 43 having a frame shape and a second region 44 surrounded by and adjacent to the first region 43. The second region 44 is, in the height direction, positioned at a position that is recessed inwardly than the first region 43 (see FIG. 9B).

Further, in the width direction of the holding surface 42, the first region 43 is positioned at both end portions and the second region 44 is positioned at the central portion of the holding surface 42. Also, the second region 44 extends along the longitudinal direction of the holding surface 42 and, in the present embodiment, disposed between the first regions 43 that are placed at both end portions in the longitudinal direction of the holding surface 42 (see FIG. 9C). However, it is not limited thereto and the second region 44 may extend from one end in the longitudinal direction to the other end in the longitudinal direction of the holding surface 42 (i.e., the first region 43 does not exist at both end portions in the longitudinal direction of the holding surface 42).

The holding palette 41 holds the absorbent main body 2 by holding the thin portion 2b of the absorbent main body 2, the thin portion 2b having a thinner thickness, on the first region 43 by suction and holding the raised portion 2a on the second region 44, the raised portion 2a having a thickness greater than the thickness of the thin portion 2b in the thickness direction, by suction. That is to say, upon receiving the absorbent main body 2, the holding palette 41 holds the absorbent main body 2 in such a manner that the thicker raised portion 2a is fitted inside the recessed space Sa formed in the second region 44. As a result, the absorbent main body 2 can be held at the holding surface 42 while keeping the reverse-side surface 2d of the absorbent main body 2 substantially flat (specifically, so as to bend arcuately along the ridge lines in the longitudinal direction of the holding surface 42). Such an effect will be explained in detail later under the heading of Effectiveness of the Present Embodiment.

In the present embodiment, a portion corresponding to the second region 44 of the holding surface 42 is recessed inwardly in the height direction of the holding palette 41 (bottom side of the holding palette 41) in such a manner that a level difference h is created between the first region 43 and the second region 44. However, it is not limited thereto and, for example, by attaching a level-raising member such as a thin plate to a region of the outer surface of the holding palette 41 corresponding to the first region 43, the surface of the level-raising member may be the first region 43 and a region of the outer surface of the holding palette 41 where the level-raising member is not attached may be the second region 44.

Further, in order to effectively produce an effect of flattening the reverse-side surface 2d of the absorbent main body 2, it is preferable that the level difference h between the first region 43 and the second region 44 is greater than or equal to the thickness difference between the raised portion 2a and the thin portion 2b. Particularly, in the present embodiment, since the level difference h is substantially equal to the thickness difference (see FIG. 9B), an effect of flattening the reverse-side surface 2d of the absorbent main body 2 can be effectively produced. Here, the level difference h means a drop in the height direction of the holding palette 41 between the position of the first region 43 and the position of the region that is recessed most inwardly in the second region 44. Further, the thickness difference means a difference in the thickness direction of the absorbent main body 2 between the thickness of the thin portion 2b and the thickness of a portion having the greatest thickness in the raised portion 2a.

Also, in the present embodiment, in order to further effectively produce the effect of flattening the reverse-side surface 2d of the absorbent main body 2, the holding palette 41 holds the absorbent main body 2 in such a manner that the raised portion 2a is accommodated inside an outer edge 44a of the second region 44. Explaining in detail, the second region 44 has a planar size greater than that of an outer shape of the raised portion 2a (specifically, an outer shape of the absorbent body 5) (see FIG. 9A).

Also, in the present embodiment, as shown in FIG. 9C, each end portion 44b of the second region 44 in the width direction of the holding surface 42 is an inclined surface that is inclined in such a manner that the height (height in the height direction of the holding palette 41) becomes greater towards an end in the width direction. That is to say, a width of opening (a length in the width direction of the holding surface 42) of the recessed space Sa becomes greater as it approaches from the inside towards the outside in the height direction of the holding palette 41. Accordingly, while properly holding the absorbent main body 2 at the holding surface 42, the absorbent main body 2 can be smoothly delivered (transferred) to the bands 3, 4 at the time of transfer. Explaining in detail, in a case where each end portions 44b in the width direction of the second region 44 is not an inclined surface, the raised portion 2a will be caught at a border between the first region 43 and the second region 44 at the time of transfer and thus the delivery of the absorbent main body 2 may not be carried out smoothly. On the other hand, in a case where each both end portion 44b of the second region 44 is an inclined surface, the raised portion 2a can be prevented from being caught at such boundary and thus a smooth delivery (transfer) of the absorbent main body 2 can be achieved.

Also, as has been described above, the plurality of holes 42a (vent holes) are formed on the entire surface of the holding surface 42 and the suction mechanism 46 draws the air through the holes 42a in order that each of the holding palettes 41 holds the thin portion 2b on the first region 43 by suction and holds the raised portion 2a on the second region 44 by suction. In the present embodiment, among the plurality of holes 42a, a size (bore diameter) of the hole 42a formed in the second region 44 is smaller than a size of the hole 42a formed in the first region 43. Thereby, a suction force (suction pressure per unit area) exerted on the raised portion 2a during the suction operation becomes smaller than a suction force exerted on the thin portion 2b. As a result, during the transfer, the absorbent main body 2 can be smoothly delivered (transferred) to the bands 3, 4, while properly holding the absorbent main body 2 on the holding surface 42.

Explaining in detail, when the absorbent main body 2 is being held on the holding palette 41, as the suction force exerted on the raised portion 2a becomes greater, it becomes more difficult for the raised portion 2a to be extracted from the recessed space Sa. Therefore, the suction force exerted on the raised portion 2a needs to be suppressed to such a degree that the raised portion 2a on the second region 44 can be held by suction and can be easy extracted from the recessed space Sa at the time of transfer. Accordingly, in the present embodiment, the size of the hole 42a formed in the second region 44 is configured to be smaller than the size of the hole 42a formed in the first region 43. It is to be noted that, in order to obtain a similar effect, the number of holes 42a formed in the second region 44 may, for example, be less than the number of holes 42a formed in the first region 43.

<<Operation of Each Section of Transfer Unit 33 in Transfer Step>>

Next, regarding the operation of each section of the transfer unit 33 in the transfer step, the behavior of the holding palette 41 and the transfer drum 45 will mainly be explained.

While the diaper manufacturing apparatus 30 is operating, the transfer drum 45 constantly rotates about the axis of rotation Ct and thus each holding palette 41 orbits along the circumferential track Tr. During this, from the absorbent main body manufacturing step, the continuous body 18 of the absorbent main body 2 is supplied towards the cutting mechanism. 47, the above-mentioned continuous body 18 is cut into a product unit by the cutting mechanism 47, and thus the absorbent main body 2 is sequentially produced by being divided.

Then, each holding palette 41 receives the absorbent main body 2 from the cutting mechanism 47 at the receiving position Qin on the circumferential track Tr and holds it on the holding surface 42. That is to say, at the transfer unit 33, a step of causing the holding palette 41 to hold the absorbent main body 2 on the holding surface 42 is performed. In this step, the absorbent main body 2 is held by the holding palette 41 by causing the suction mechanism 46 to perform a suction operation in such a manner that the thin portion 2b of the absorbent main body 2 is held by suction on the first region 43 of the holding surface 42 and the raised portion 2a is held by suction on the second region 44.

Also, as has been described above, at the receiving position Qin, the holding palette 41 is in a state where the longitudinal direction of the holding surface 42 lies along the MD-direction. (In other words, a state in which the width direction of the holding surface 42 lies along the axial direction of the axis of rotation Ct of the transfer drum 45 (i.e., axis of rotation direction which is CD-direction in the present embodiment)). As a result, the holding palette 41 receives the absorbent main body 2 in a state where the longitudinal direction of the holding surface 42 and the longitudinal direction of the absorbent main body 2 lies along each other and the absorbent main body 2 is held by the holding surface 42 in such a state.

The holding palette 41 that has passed the receiving position Qin is directed to the transferring position Qout while holding the absorbent main body 2 on the holding surface 42. At this time, as has been described above, since the reverse-side surface 2d (a surface located at an outermost position in the radial direction of the transfer drum 45) which is the transfer surface of the absorbent main body 2 is substantially flat, the moving velocity (rotational velocity) of the reverse-side surface 2d is maintained at a uniform velocity for the entire length in its direction of movement (i.e., circumferential direction of the transfer drum 45).

Then, the holding palette 41 pivots through 90 degrees about the pivotal axis Cs while orbiting along the circumferential track Tr from the receiving position Qin towards the transferring position Qout. Thus, the absorbent main body 2 held on the holding palette 41 changes from a state in which its longitudinal direction lies along the MD-direction to a state in which it lies along the CD-direction and maintains this state until it reaches the transferring position Qout. It is to be noted that, while pivoting through 90 degrees about the pivotal axis Cs, the holding palette 41 relatively moves with respect to the transfer drum 45 in the same direction as the rotational direction of the transfer drum 45 in such a manner that the distance from the subsequent holding palette 41 becomes greater in order to prevent an intervention with the subsequent holding palette 41 adjacent thereto on an upstream side in its direction of movement (circumferential direction of the transfer drum 45) (see FIG. 8).

Thereafter, when the holding palette 41 reaches the transferring position Qout, the absorbent main body 2 is delivered and transferred from the holding surface 42 to the pair of bands 3, 4 at this position Qout. At the transferring position Qout, the holding palette 41 is in a state where the longitudinal direction of the holding surface 42 lies along the CD-direction (in other words, in a state where the width direction of the holding surface 42 lies along the circumferential direction of the transfer drum 45 (MD-direction)). As a result, the absorbent main body 2 will be delivered to the pair of bands 3, 4 in a state where its longitudinal direction lies along the CD-direction. That is to say, the absorbent main body 2 bridges the bands 3 and 4 in such a manner that the absorbent main body 2 (the longitudinal direction of the absorbent main body 2) is orthogonal to the pair of bands 3, 4 transported in the MD-direction.

As has been described above, at the transfer unit 33, a step of transferring the absorbent main body 2 to the bands 3, 4 by moving the holding palette 41 that is holding the absorbent main body 2 towards the bands 3, 4 is performed.

It is to be noted that, when the holding palette 41 reaches the transferring position Qout, first, one end portion in the intersecting direction of the reverse-side surface 2d of the absorbent main body 2 opposes the bands 3, 4 at the transferring position Qout and then the other end portion in the intersecting direction opposes the bands 3, 4 at the same position Qout. Here, since the reverse-side surface 2d of the absorbent main body 2 that is in the state of being held on the holding palette 41 is substantially flat, each end portion in the intersecting direction of the reverse-side surface 2d will come into contact with and attached to the bands 3, 4 with an appropriate contact pressure when it passes the transferring position Qout and opposes the bands 3, 4. That is, in the present embodiment, the absorbent main body 2 (specifically, both end portions in the intersecting direction of the reverse-side surface 2d) can be securely contacted with predetermined portions of the bands 3, 4 and joined to such portions by causing the transfer drum 45 to rotate and by causing the holding palette 41 holding the absorbent main body 2 to reach at the transferring position Qout.

Thereafter, the holding palette 41 pivots again through 90° (degrees) about the pivotal axis Cs to bring the longitudinal direction of the holding palette 41 back from the CD-direction to the MD-direction and thereby prepares for receiving the absorbent main body 2 at the receiving position Qin. It is to be noted that, when pivoting through 90° (degrees) about the pivotal axis Cs again, the holding palette 41 relatively moves with respect to the transfer drum 45 in order to avoid interfering with the holding palette 41 that is adjacent in its direction of movement (circumferential direction of the transfer drum 45) (see FIG. 8).

Effectiveness of the Present Embodiment

According to the diaper manufacturing apparatus 30 and the method of manufacturing the diaper 1 of the present embodiment, it is possible to prevent roughness from occurring in the transfer surface (i.e., reverse-side surface 2d) of the absorbent main body 2 in a state where the absorbent main body 2 (first material) is held on the holding palette 41 (holding body) and to properly perform the subsequent transfer step. In the following, the effectiveness of the present embodiment will be described.

Figure 10A:
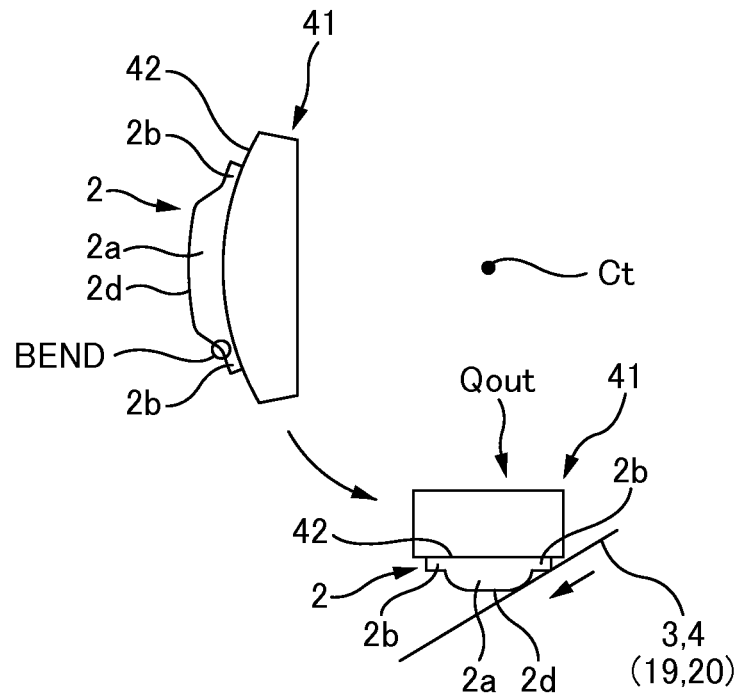
FIGS. 10A and 10B are explanatory diagrams related to an effectiveness of the present embodiment.

As has been described above under the heading of Problem to be Solved by the Invention, some of the absorbent main bodies 2 may have portions that have different thicknesses with each other in the thickness direction (i.e., the raised portion 2a and the thin portion 2b). When holding such absorbent main body 2 on the holding palette 41, if, for example, the absorbent main body 2 is placed on the flat holding surface 42, as shown in FIG. 10A, unevenness such as creases and bends will occur in the transfer surface of the absorbent main body 2. FIG. 10A is a diagram showing a comparison example for explaining the effectiveness of the present embodiment and is a diagram showing how the absorbent main body 2 is placed on a flat holding surface 42.

The above-mentioned unevenness is due to the thickness difference between the raised portion 2a and the thin portion 2b. That is to say, if the absorbent main body 2 on which both the raised portion 2a and the thin portion 2b exist is placed on the flat holding surface 42, bends and creases will occur near the border position between the raised portion 2a and the thin portion 2b and an unevenness will be produced as shown in FIG. 10A. Then, if the absorbent main body 2 is moved to the transferring position Qout with the unevenness remaining on the reverse-side surface 2d corresponding to the transfer surface, the absorbent main body 2 may not be properly transferred to the bands 3, 4 (second material).

Further, a gap between the holding surface 42 and the bands 3, 4 at the transferring position Qout needs to be set in such a manner that the absorbent main body 2 comes into contact with the bands 3, 4 with a proper contact pressure at such position Qout, and in a case where the holding surface 42 is a flat surface, it will be set by taking the raised portion 2a of a thicker thickness in the absorbent main body 2 as a reference. In such a case, while the raised portion 2a can come into contact with the bands 3, 4 with a sufficient contact pressure, the thin portion 2b having a thinner thickness cannot come into contact with the bands 3, 4 with a sufficient contact pressure and thus there will be a portion that is not properly adhered to the bands 3, 4 (see FIG. 10A).

Further, in the case of transferring the absorbent main body 2 having a gathering portion (specifically, the leg-surrounding gathering portion 12) formed thereon at the thin portion 2b by the stretchable member 11, the transferring will become even more difficult if the holding surface 42 is a flat surface. That is to say, when the absorbent main body 2 is placed on the flat holding surface 42, the stretchable member 11 extended along the longitudinal direction of the absorbent main body 2 will contract and thus there will be pleats-like creases from the thin portion 2b to the raised portion 2a. With regards to the absorbent main body 2 with creases, it is difficult to transfer properly.

Figure 10B:
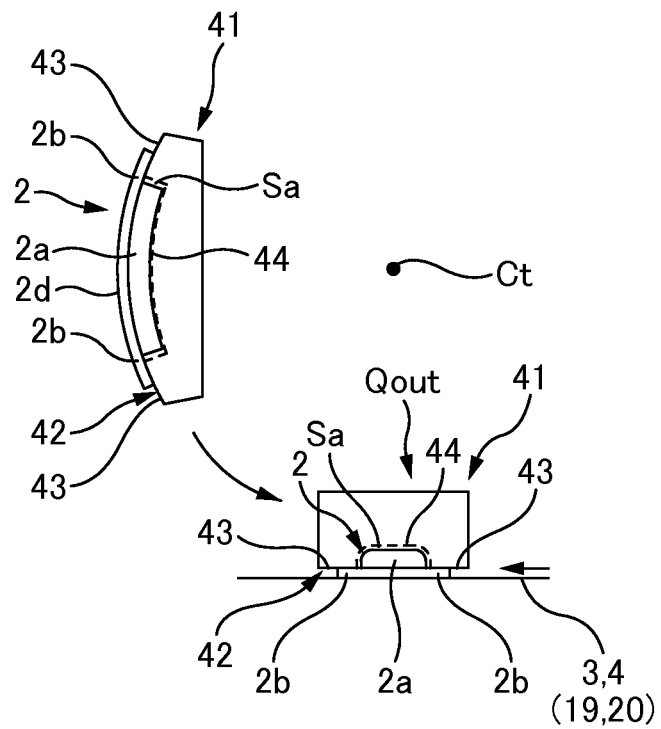

Regarding the disadvantages described above, in the present embodiment, the holding surface 42 includes the first region 43 and the second region 44 that is positioned at a position recessed inwardly than the first region 43 in the height direction of the holding palette 41. The holding palette 41 holds the absorbent main body 2 while holding the thin portion 2b of the absorbent main body 2 on the first region 43 by suction and holding the raised portion 2a on the second region 44 by suction. In other words, the absorbent main body 2 is held in such a manner that the raised portion 2a fits into the recessed space Sa formed on the second region 44. Thus, since the level difference between the first region 43 and the second region 44 compensates for the thickness difference between the raised portion 2a and the thin portion 2b, occurrence of unevenness on the reverse-side surface 2d corresponding to the transfer surface can be suppressed and, as shown in FIG. 10B, the absorbent main body 2 can be held on the holding surface 42 while keeping the reverse-side surface 2d substantially flat. FIG. 10B is an explanatory diagram illustrating the effectiveness of the present embodiment and shows that the absorbent main body 2 is held on the holding surface 42 of the present embodiment.

Also, as has been described above, since the reverse-side surface 2d of the absorbent main body 2 that is being held on the holding palette 41 is substantially flat, a region of the reverse-side surface 2d which opposes the bands 3, 4 comes into contact with the bands 3, 4 for the entire region (all of the portions attached to the bands 3, 4 properly come into contact with the bands 3, 4) with an appropriate contact pressure. That is to say, in the present embodiment, by causing the transfer drum 45 to rotate and thus causing the holding palette 41 that holds the absorbent main body 2 to come to the transferring position Qout, the absorbent main body 2 can be securely contacted with predetermined positions on the bands 3, 4 and joined to such portions. As has been described above, according to the present embodiment, when the absorbent main body 2 having portions with different thicknesses is held on the holding palette 41, it can be held in such a manner that the subsequent transferring can be performed properly.

Also, in the present embodiment, the thin portion 2b is positioned at each end portion in the width direction of the thin portion 2b, the raised portion 2a is positioned at the central portion in the width direction of the absorbent main body 2, the absorbent body 5 is positioned on the raised portion 2a, and the stretchable member 11 for forming the gathering portion (leg-surrounding gathering portion 12) is attached to the thin portion 2b along the longitudinal direction of the absorbent main body 2. The first region 43 is positioned at each end portion in the width direction of the holding surface 42, the second region 44 is positioned at the central portion in the width direction of the holding surface 42 and the holding palette 41 holds the absorbent main body 2 in such a manner that the width direction of the holding surface 42 lies along the intersecting direction of the absorbent main body 2. In such a case, the effect of the present invention will become more significant.

That is to say, as has been described above, in the case of transferring the absorbent main body 2 with the above-mentioned gathering portion being formed on the thin portion 2b by the stretchable member 11, if the holding surface 42 is flat and the absorbent main body 2 is held on such holding surface 42, pleats-like creases will be produced in the absorbent main body 2 due to contraction of the stretchable member 11 and thus the subsequent transferring becomes difficult. On the contrary, according to the structure of the present invention, since the raised portion 2a will fit into the recessed space Sa when the absorbent main body 2 is held on the holding surface 42, the stretching of the stretchable member 11 and the resulting contracting of the absorbent main body 2 will be restricted and thus the above-mentioned creases can be prevented from occurring. As a result, the absorbent main body 2 with the gathering portion being formed thereon by the stretchable member 11 can also be appropriately transferred.

Also, with the level difference h between the first region 43 and the second region 44 being greater than or equal to the thickness difference between the raised portion 2a and the thin portion 2b, the reverse-side surface 2d of the absorbent main body 2 can be easily made flat and the absorbent main body 2 can be appropriately transferred to the bands 3, 4. Further, it is preferable that the above-mentioned level difference h and the above-mentioned thickness difference are generally equal as in the present embodiment. However, it is not limited thereto and the above-mentioned level difference h may be less than the thickness difference between the raised portion 2a and the thin portion 2b.

Also, with the second region 44 having a planar size greater than or equal to that of the contour of the raised portion 2a as in the present embodiment, it becomes easier to flatten the reverse-side surface 2d of the absorbent main body 2 and the absorbent main body 2 can be further properly transferred to the bands 3, 4. That is to say, in a case where the holding palette 41 holds the absorbent main body 2 in a state where raised portion 2a is accommodated inside the outer edge 44a of the second region 44, the effect of the present invention can be produced effectively. It is to be noted that, preferably, the planar size of the second region 44 is generally the same as that of the contour of the raised portion 2a (specifically, the contour of the absorbent body 5).

===Variant of the Transfer Step===

In the above described embodiment of the transfer step (hereinafter referred to as the example of the present invention), the holding palette 41 pivots through 90 degrees about the pivotal axis Cs while moving from the receiving position Qin to the transferring position Qout. That is to say, in the example of the present invention, at the receiving position Qin, the holding palette 41 is in a state where the width direction of the holding surface 42 lies along the axial direction of the axis of rotation Ct of the transfer drum 45 (CD-direction) and, at the transferring position Qout, the holding palette 41 is in a state where the width direction lies along the circumferential direction of the transfer drum 45. As a result, when the absorbent main body 2 corresponding to the first material is being transferred to the bands 3, 4 corresponding to the second material, the longitudinal direction of the absorbent main body 2 will be orthogonal to the continuous direction (transport direction) of the bands 3, 4.

Figure 11A:
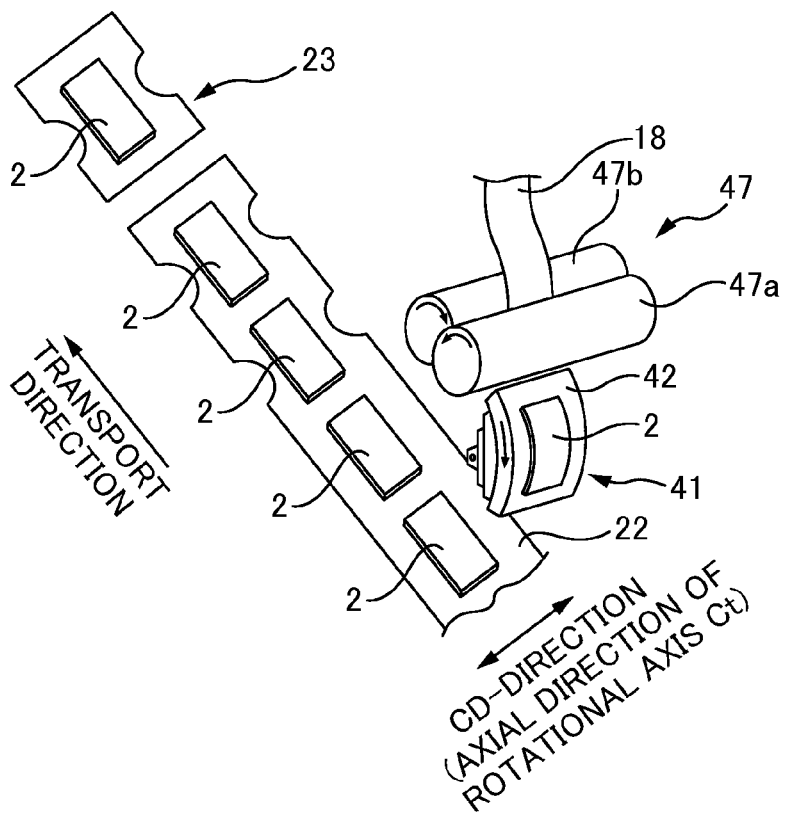
FIGS. 11A and 11B are diagrams showing a variant of the transfer step.
Figure 11B:
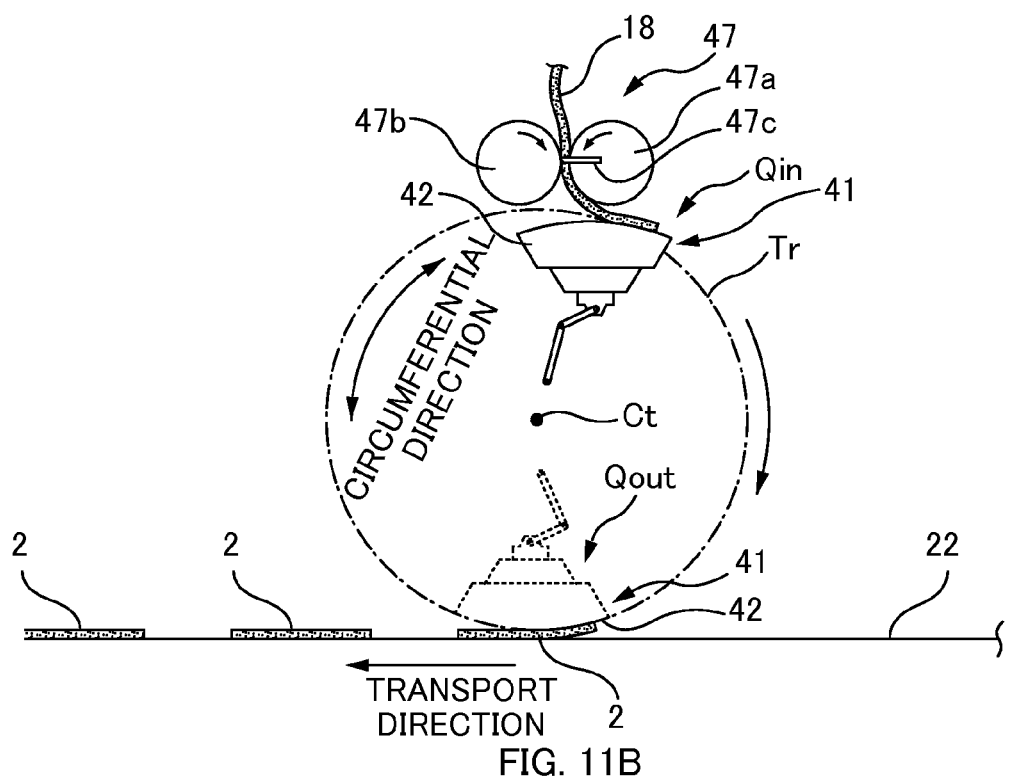

It is to be noted that, the above described embodiment of the transfer step is shown byway of example and other embodiments (hereinafter referred to as a variant) may also be conceived. Hereinafter, the variant of the transfer step will be described with reference to FIGS. 11A and 11B. FIGS. 11A and 11B are diagrams showing the variant of the transfer step. In order to facilitate the explanation, only one of the holding palettes 41 is shown in FIGS. 11A and 11B.

<<Structure of Variant>>

In the variant, as shown in FIG. 11A, the absorbent main body 2 is transferred to a wide band-like member 22. In other words, the band-like member 22 is a continuous sheet corresponding to the second material of the variant. As shown in FIG. 11A, the band-like member 22 is transported along its continuous direction and the absorbent main body 2 is transferred (joined) in such a manner that its longitudinal direction lies along the transport direction (MD-direction) of the band-like member 22. The band-like member 22 to which the absorbent main body 2 is joined is cut into a form of a product in a step-by-step manner and will form a semi-product diaper 23 (the diaper 1 before being completed as a product) in a spread out fashion by being severed at a regular interval in the transport direction.

As has been described above, in contrast to the example of the present invention in which the back-side band 3 and the stomach-side band 4 are separate and the absorbent main body 2 bridges the bands 3, 4, according to the variant, a portion corresponding to the back-side band 3 and a portion corresponding to the stomach-side band 4 are connected into a single sheet and is joined to a central portion in the width direction of the band-like member 22 (direction intersecting with the continuous direction).

In order to perform the transferring of the above-mentioned form, according the variant, the holding palette 41 is, at the receiving position Qin, in a state where the width direction of the holding surface 42 lies along the axial direction of the axis of rotation Ct of the transfer drum 45 (CD-direction) and moves to the transferring position Qout while keeping such a state (see FIG. 11B). That is to say, regarding the holding palette 41 according to the variant, a 90-degree pivot during the movement from the receiving position Qin to the transferring position Qout is not performed and the transferring is performed in a state where the width direction of the holding surface 42 is kept in the CD-direction. As a result, the absorbent main body 2 is transferred to the band-like member 22 in a state where its longitudinal direction lies along the transport direction of the band-like member 22 (MD-direction).

The example of the present invention and the variant differ for the above-mentioned points, but they are generally similar for other points and the variant also produces an effect similar to that of the present invention.

Difference in Effect Between Example of Present Invention and Variant

Figure 12A:
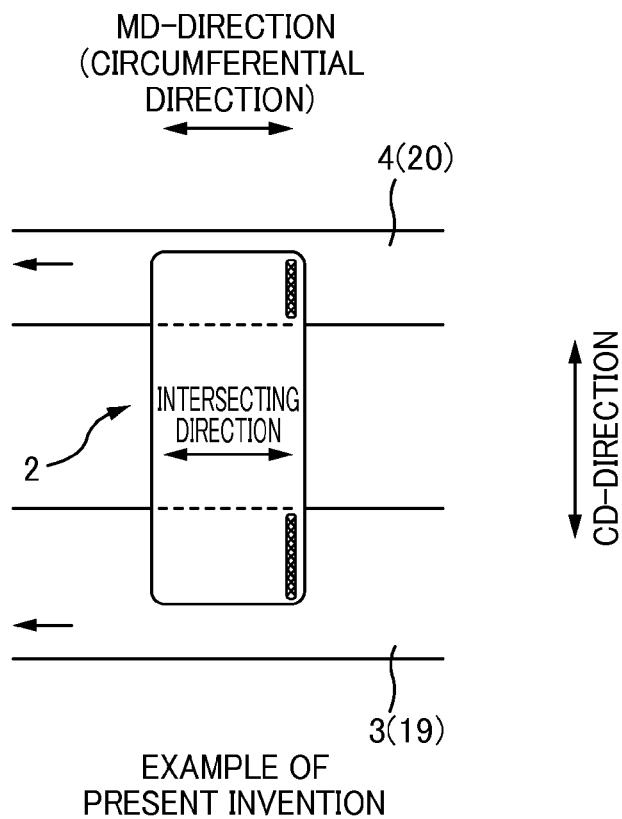
FIGS. 12A and 12B are diagrams showing differences of the effects between the present example and the variant.
Figure 12B:
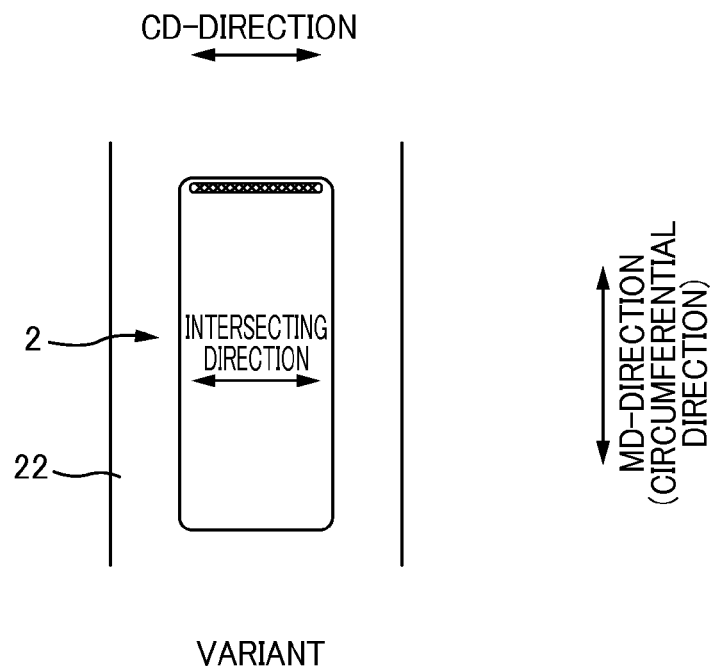

As has been described above, in the example of the present invention, the transferring is performed in a state where the width direction of the holding surface 42 lies along the circumferential direction of the transfer drum 45 and, in the variant, the transferring is performed in a state where the above-mentioned width direction lies along the axial direction of the axis of rotation Ct of the transfer drum 45. As a result, as shown in FIGS. 12A and 12b, according to the example of the present invention, a portion (a hatched portion in the drawing) of the absorbent main body 2 that is transferred to the second material (bands 3, 4 or band-like member 22) at the beginning of the transferring is wider as compared to the variant. FIGS. 12A and 12B are explanatory diagrams showing differences of the effects between the present example and the variant. FIG. 12A shows the example of the present invention and FIG. 12B shows the variant. That is to say, since the region transferred at the beginning of the transferring is wider in the present invention as compared to the variant, the effect of the present invention directed to holding the absorbent main body 2 for an appropriate transferring will be more significant. In this aspect, the example of the present invention is preferable as compared to the variant.

Other Embodiments

In the above-mentioned various embodiments, the diaper manufacturing apparatus 30 and the method of manufacturing the diaper 1 of the present invention have been mainly discussed. However, the above-mentioned embodiments are provided for the purpose of facilitating the understanding of the present invention only and do not give any limitation to the present invention. It goes without saying that any modifications and improvements to the present invention can be made without departing from the spirit of the invention and the present invention includes its equivalents.

Further, the above-mentioned settings, dimensions, configurations, etc., are merely examples to show effectiveness of the present invention and should not be understood as any limitation to the present invention. Particularly, the configuration of the absorbent main body 2 is not limited to the above-mentioned embodiment and, for example, not limited with regard to the placement of the thin portion 2b corresponding to the first portion and the raised portion 2a corresponding to the second portion. Also, with regards to the configuration of the holding surface 42, the placement of the first region 43 and the second region 44 is not limited to the above-mentioned embodiment and may be a placement that corresponds to the placement of the raised portion 2a and the thin portion 2b in the absorbent main body 2.

Also, in the above-mentioned embodiment, the absorbent main body 2 having the absorbent body 5 and the gathering portion formed on both sides of the absorbent body 5 (leg-surrounding gathering portion 12) has been described as an example of the first material, but it is not limited thereto. The gathering portion may not be formed on the absorbent main body 2 before the transferring or the above-mentioned gathering portion may not be formed on the absorbent main body 2 even at the time the product has been finished. Also, as long as portions having different thicknesses with respect to each other in the thickness direction are provided (exist at the same time), it may be the first material other than the absorbent main body 2.

Also, in the above-mentioned embodiment, the transfer drum 45 has been explained as an example of the transfer section. That is to say, an explanation has been made for a case in which the holding palette 41 that holds the absorbent main body 2 orbits along the circumferential track Tr by the rotation of the transfer drum 45. However, the transfer section is not limited to the transfer drum 45 and, for example, may be something that causes the holding palette 41 to move linearly along a linear track such as a belt conveyor.

Also, in the above-mentioned embodiment, the diaper 1 has been taken as an example of the absorbent article and the manufacturing apparatus and method thereof have been described. However, it is not limited thereto, and, for example, other absorbent articles include sanitary napkins, incontinence pad and wiper and the present invention is also applicable to a manufacturing apparatus and method thereof.

LIST OF REFERENCE NUMERALS 1 diaper (absorbent article), 1a waist opening, 1b leg opening,
2 absorbent main body (first material),
2a raised portion (second portion), 2b thin portion (2b first portion),
2c skin-side surface, 2d reverse-side surface,
3 back-side band (second material), 4 stomach-side band (second material),
5 absorbent body, 6 front surface sheet, 7 back surface sheet,
8 exterior sheet, 9 absorbent body core, 10 thin paper,
11 stretchable member, 12 leg-surrounding gathering portion,
13 three-dimensional gathering portion,
14 rubber member, 15 diaper continuous body, 16 diaper continuous body piece,
17 pre-split continuous band, 18 continuous body,
19 continuous band, 20 continuous band,
21 arch, 22 band-like member (second material),
23 semi-product diaper,
30 diaper manufacturing apparatus (absorbent article manufacturing apparatus),
31 absorbent main body manufacturing unit, 32 band transport unit,
33 transfer unit, 34 product-cutting unit, 35 splitter,
41 holding palette (holding body), 42 holding surface, 42a hole,
43 first region, 44 second region, 44a outer edge, 44b both end portions,
45 transfer drum (transfer section), 46 suction mechanism,
47 cutting mechanism, 47a roller, 47b roller, 47c flat blade,
Qin receiving position, Qout transferring position,
Cc1 axis, Cc2 axis, Cs pivotal axis, Ct axis of rotation,
S accommodating space, Sa recessed space, Tr circumferential track

The invention claimed is:

1. An apparatus for manufacturing an absorbent article having a first material and a second material, in combination with the absorbent article, the apparatus comprising:
a holding body that includes a holding surface and that holds the first material with the holding surface; and
a transfer section that transfers the first material to the second material by moving the holding body, the holding body holding the first material, to the second material,
wherein the first material has a first portion and a second portion, the second portion having a thickness greater than that of the first portion in a thickness direction of the first material,
wherein the holding surface has a first region and a second region, the second region being located at a portion that is more recessed to an inner side than the first region in a height direction of the holding body, and
wherein the holding body holds the first material by causing the first portion to be held by suction on the first region and causing the second portion to be held by suction on the second region,
wherein a suction pressure per unit area exerted on the second portion during suction operation is smaller than a suction pressure per unit area exerted on the first portion during the suction operation, and
wherein
the first material includes a stretchable member, and
the first portion holds the stretchable member in an extended state along a longitudinal direction of the first material.

2. The apparatus for manufacturing the absorbent article in combination with the absorbent article according to claim 1,
wherein the absorbent article includes an absorbent main body as the first material,
wherein the absorbent main body includes an absorbent body and a gathering portion that is formed on each side of the absorbent body,
wherein, in an intersecting direction that intersects with a longitudinal direction of the absorbent main body, the first portion is located at each end portion of the absorbent main body and the second portion being located at a central portion of the absorbent main body,
wherein the absorbent body is disposed at the second portion,
wherein the stretchable member is attached to the first portion along the longitudinal direction for forming the gathering portion,
wherein, in a width direction of the holding surface, the first region is located at both end portions of the holding surface and the second region being located at a central portion of the holding surface, and
wherein the holding body holds the absorbent main body in such a manner that the width direction lies along the intersecting direction.

3. The apparatus for manufacturing the absorbent article in combination with the absorbent article according to claim 2,
wherein the second portion extends along the longitudinal direction,
wherein the transfer section comprises a transfer drum that rotates while supporting the holding body,
wherein the transfer drum rotates to thereby move the holding body from a receiving position at which the holding body receives the absorbent main body with the holding surface to a transfer position at which the absorbent main body held by the holding body is transferred to the second material, and
wherein the holding body is provided in such a manner that, at the receiving position, the width direction lies along an axis of rotation of the transfer drum, and, at the transfer position, the width direction lies along a circumferential direction of the transfer drum.

4. The apparatus for manufacturing the absorbent article in combination with the absorbent article according to claim 2, wherein a level difference between the first region and the second region is greater than or equal to a thickness difference between the first portion and the second portion.

5. The apparatus for manufacturing the absorbent article in combination with the absorbent article according to claim 2, wherein the holding body holds the absorbent main body in such a manner that the second portion is placed inside an outer edge of the second region.

6. The apparatus for manufacturing the absorbent article in combination with the absorbent article according to claim 2, wherein each end portion of the second region in the width direction is inclined in such a manner that a length in the height direction becomes greater as each end portion of the second region gets nearer to an end in the width direction.

7. The apparatus for manufacturing the absorbent article in combination with the absorbent article according to claim 1,
wherein the holding surface has a plurality of holes formed therein,
wherein a suction mechanism is provided, the suction mechanism being configured to suck the air through the holes in order that the holding body causes the first portion to be held by suction to the first region and causes the second portion to be held by suction to the second region, and
wherein, among the plurality of holes, holes formed in the second region has a size that is smaller than a size of holes formed in the first region.

8. The apparatus for manufacturing the absorbent article in combination with the absorbent article according to claim 1, wherein
a cutting mechanism for forming the first material by cutting a continuous body of the first material is provided, and
the holding body receives the first material from the cutting mechanism.

* * * * *